United States Patent
Walker et al.

(10) Patent No.: US 12,083,125 B2
(45) Date of Patent: *Sep. 10, 2024

(54) DRUG-INDUCED EPIGENETIC REMODELING TO PREVENT FIBROSIS

(71) Applicant: Thomas Jefferson University, Philadelphia, PA (US)

(72) Inventors: Janice L. Walker, Philadelphia, PA (US); Alexander Mazo, Cherry Hill, NJ (US); Svetlana Petruk, Voorhees, NJ (US); A. Sue Menko, Merion Station, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/859,082

(22) Filed: Jul. 7, 2022

(65) Prior Publication Data
US 2022/0401454 A1    Dec. 22, 2022

Related U.S. Application Data

(63) Continuation of application No. 16/335,716, filed as application No. PCT/US2017/053249 on Sep. 25, 2017, now Pat. No. 11,400,099.

(60) Provisional application No. 62/398,926, filed on Sep. 23, 2016.

(51) Int. Cl.
*A61K 31/55* (2006.01)
*A61K 9/00* (2006.01)

(52) U.S. Cl.
CPC ............ *A61K 31/55* (2013.01); *A61K 9/0014* (2013.01); *A61K 9/0048* (2013.01); *A61K 9/0051* (2013.01)

(58) Field of Classification Search
CPC .... A61K 31/55; A61K 9/0014; A61K 9/0048; A61K 9/0051
See application file for complete search history.

(56) References Cited

U.S. PATENT DOCUMENTS 11,400,099 B2 *   8/2022   Walker ................ A61K 9/0051
2011/0256054 A1  10/2011  Menko et al.
2016/0025745 A1   1/2016   Guo et al.

FOREIGN PATENT DOCUMENTS

WO          2012052390 A1     4/2012

OTHER PUBLICATIONS

Tocris GSK-J5 product label (Year: 2017).*
MCE GSK-J2 Product data sheet (Year: 2023).*
Kruidenier et al. Nature, Aug. 16, 2012;488(7411):404-8. (Year: 2012).*
Yap, et al. "HSK27me3 demethylases regulate in vitro chondrogenesis and chondrocyte activity in osteoarthritis", Arthritis Research & Therapy. Jul. 7, 2016 vol. 18, p. 1-10; p. 2, left col. para 2, right col. para 4, abstract.
Faralli, et al. "UTX demethylase activity is required for satellite cell-mediated muscle regeneration", The Journal of Clinical Investigation, Apr. 1, 2016 vol. 126, p. 1555-1565; entire document.
Morozov, et al. "Inhibitor of H3K27 demethylase JMJD3/UTX GSK-J4 is a potential therapeutic option for castration resistant prostate cancer", Oncotarget Jul. 8, 2017 vol. 8, p. 62131-52142; entire document.
International Search Report dated Dec. 11, 17 for PCT/US17/053249.

* cited by examiner

*Primary Examiner* — Kara R Mcmillian
(74) *Attorney, Agent, or Firm* — Riverside Law LLP

(57) ABSTRACT

A therapeutic treatment for preventing or reducing the formation of fibrosis comprising administering to a patient a UTX or JMJD3 inhibitor that are effective in preventing or reducing fibrosis in situations wherein access to an injury or dysmorphogenetic tissues before the fibrotic process becomes established in the tissues.

19 Claims, 21 Drawing Sheets

Ex vivo Mock Cataract Surgery Model

DRUG-INDUCED EPIGENETIC REMODELING TO PREVENT FIBROSIS

CROSS REFERENCE TO RELATED APPLICATIONS

This application is a continuation of U.S. patent application Ser. No. 16/335,716 filed Mar. 22, 2019, and issued as U.S. Pat. No. 11,400,099 on Aug. 2, 2022, which claims the benefit of International Patent Application No. PCT/US17/53249, filed Sep. 25, 2017, published as WO 2018/058034 on Mar. 29, 2018, which claims benefit to U.S. Provisional Application Ser. No. 62/398,926, filed Sep. 23, 2016, the disclosure contents of which are hereby incorporated by reference in their entirety.

STATEMENT REGARDING FEDERALLY SPONSORED RESEARCH OR DEVELOPMENT

This invention was made with government support under R01EY026159 awarded by the National Institutes of Health. The government has certain rights in the invention.

FIELD OF INVENTION

The present invention is generally related to blocking histone modifying activity of H3K27 demethylases, such as Ubiquitously Transcribed X Chromosome Tetratricopeptide Repeat Protein (UTX), which would allow for faster accumulation of H3K27me3 and therefore a condensed structure on chromatin on the newly replicated DNA that could prevent myofibroblast differentiation by blocking association of the master lineage-specifying transcription factor MRTFA.

BACKGROUND OF INVENTION

Most tissues of the eye are susceptible to developing fibrotic disease, blinding millions of people throughout the world. Furthermore, fibrosis can affect almost every organ of the body, thus creating a disease profile that affects tens of millions of people worldwide. Despite the far reaching effects of fibrosis, there are no effective approaches to prevent, slow or reverse this disease process. The cell type responsible for causing fibrotic disease is the myofibroblast. Understanding how a cell acquires an altered heritable phenotype to become a myofibroblast, leading to fibrotic scarring associated with this pathological disease process, is a key question, likely to provide essential clues toward developing anti-fibrotic therapeutics, which remains unanswered.

Changing transcriptional programming during reprogramming of a cell to a myofibroblast is not well understood. In major aspects, it has to rely on changes in the epigenetic mechanisms of inheritance of chromatin structure during DNA replication. The mechanism of epigenetic inheritance during cell proliferation remains unknown, and we know even less about how epigenetic information and the corresponding transcriptional programs change during cell reprogramming. The gaps in our knowledge of these essential biological processes are based on the lack of direct experimental approaches that would allow examining the structure of chromatin and the state of transcription during and following DNA replication during cell proliferation and cell differentiation.

How cells with a normal function are reprogrammed to become myofibroblasts, the cell type responsible for fibrotic disease, is not yet understood. Fundamental to the regulation of this cell differentiation process is uncovering how chromatin structure controls access of specific transcription factor (TFs) to DNA to coordinate changes in transcriptional programs and thus cell lineage specification.

SUMMARY OF INVENTION

De-condensed structure of nascent, post-replicative chromatin is essential for binding of lineage-specific transcription factors to repressed genes and changing of the transcriptional programs of differentiating cells. Blocking histone-modifying activity of specific enzymes has the potential to manipulate the structure of nascent chromatin. Therefore we determined that blocking the histone modifying activity of histone H3K27 trimethylase (KDM) UTX leads to a faster accumulation of H3K27me3 and therefore a much more condensed nucleosome structure on nascent DNA, and prevents binding of master lineage-specifying transcription factor MRTF-A and myofibroblast differentiation. Inhibition of UTX activity effectively prevented the emergence of αSMA+ myofibroblasts. These findings provide insight into the epigenetic events regulating cell reprogramming to a myofibroblast phenotype as well as reveal the potential to develop therapeutic strategies to modulate epigenetically-mediated cell reprogramming to treat fibrotic disease.

A method of preventing or reducing fibrosis, comprising administering to a patient a pharmaceutical composition that inhibits UTX H3K27 de-methylase activity, which would lead to closed chromatin structure on nascent DNSA, and block reprogramming to a myofibroblast phenotype, the major cell type associated with causing fibrotic disease.

The method of claim 1 wherein the H3K27 de-methylase UTX inhibitor is GSK-J4.

A method for reducing fibrosis formation comprising treatment with a H3K27 de-methylase UTX inhibitor, wherein said treatment prevented 1) α smooth muscle actin (αSMA) expression, a defining feature of myofibroblasts, in the ex vivo mock cataract surgery model and 2) expression of Fibronectin EDA (FN-EDA) and Collagen I expression, wherein said FN-EDA expression is tightly linked to myofibroblast differentiation and Collagen I is a defining feature of fibrosis/scarring.

A method of treatment of tissues before the fibrotic process establishes comprising administering to a patient treatment with a H3K27 de-methylase UTX inhibitor.

A method of treatment wherein treatment with H3K27 de-methylase UTX inhibitor can be applied at the time of cataract surgery to prevent the development of the lens fibrotic disease Posterior Capsule Opacification (PCO).

A method of preventing or reducing fibrosis, comprising administering to a patient an effective amount of a pharmaceutical composition comprising a H3K27 de-methylase UTX inhibitor.

A method of preventing or reducing fibrosis, comprising administering to a patient an effective amount of a pharmaceutical composition comprising a H3K27 de-methylase UTX inhibitor, wherein the H3K27 de-methylase UTX inhibitor is GSK-J4 or a suitable salt thereof.

A method of preventing or reducing fibrosis, comprising administering to a patient an effective amount of a pharmaceutical composition comprising a H3K27 de-methylase UTX inhibitor, wherein the H3K27 de-methylase UTX inhibitor is GSK-J4 or a suitable salt thereof, wherein the pharmaceutical composition is administered topically to a skin surface.

A method of preventing or reducing fibrosis, comprising administering to a patient an effective amount of a pharmaceutical composition comprising a H3K27 de-methylase UTX inhibitor, wherein the H3K27 de-methylase UTX inhibitor is GSK-J4 or a suitable salt thereof, wherein the pharmaceutical composition is administered topically to a skin surface, wherein the pharmaceutical composition is administered to a patient within 24 hours of a surgical procedure.

A method of treatment of a patient tissues before the fibrotic process establishes after a surgical procedure, comprising administering to said patient an effective amount of a pharmaceutical composition comprising a H3K27 de-methylase UTX inhibitor at the time of the surgical procedure. Preferably, wherein the H3K27 de-methylase UTX inhibitor is GSK-J4 or a suitable salt thereof. The route of administration may be selected by those of skill in the art based upon the injury to be treated, preferably, wherein the pharmaceutical composition is administered orally, intradermally, or topically to a skin surface.

A method of preventing or reducing the formation of fibrosis in ocular tissues after an ocular surgery comprising: administering to a patient undergoing said ocular surgery a UTX inhibitor at the time of the ocular surgery. Preferably, wherein the UTX inhibitor is GSK-J4 or a suitable salt thereof. Preferably, wherein the UTX inhibitor is administered topically to the eye.

A method of treatment of the fibrotic disease Posterior Capsule Opacification (PCO) comprising: performing a cataract surgery on a patient; and administering to said patient a sufficient amount of a UTX inhibitor during said surgery, preferably, wherein the UTX inhibitor is GSK-J4 or a suitable salt thereof, and preferably, wherein the UTX inhibitor is administered topically to the eye.

A method of treatment of the fibrotic disease Posterior Capsule Opacification (PCO) comprising: performing a cataract surgery on a patient; administering to said patient a sufficient amount of a UTX inhibitor during said surgery; and implanting an intraocular lens into the eye, wherein said intraocular lens comprises a sustained release mechanism to allow for release of the UTX inhibitor for at least 24 hours. In certain embodiments, said sustained release mechanism provides for release for between 24 and 72 hours.

DETAILED DESCRIPTION OF THE EMBODIMENTS

Figure 1:
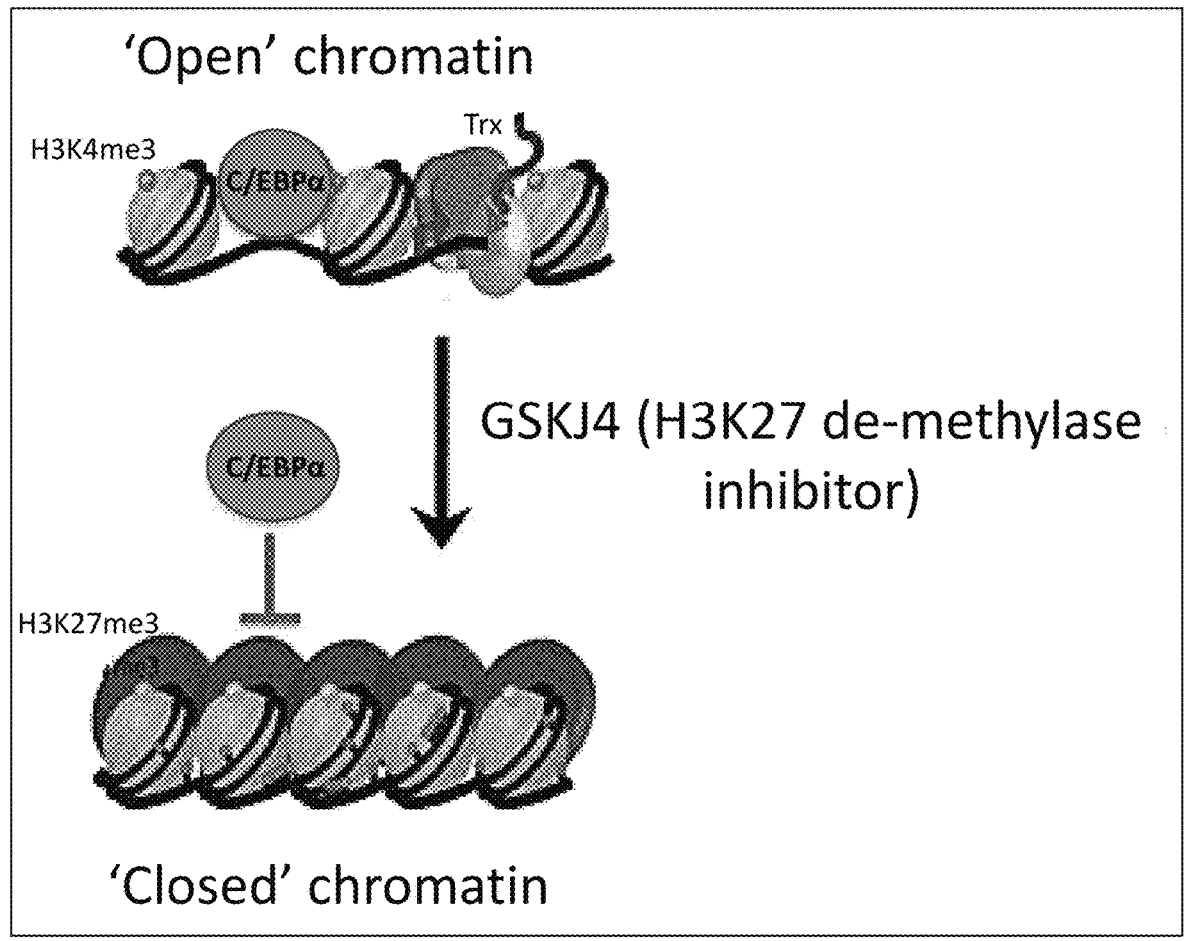
FIG. 1 depicts a model depicting how chromatin structure can be manipulated using the UTX/JMJD3 inhibitor GSK J4 to block reprogramming to a myofibroblast phenotype leading to fibrosis.

Fibrotic disease affects almost every organ of the body and is believed to result in approximately 45% of all deaths in the industrialized world. This staggering number is underscored by the fact that we have no readily available treatments or therapeutics to treat fibrosis. While all tissues can become fibrotic, the tissues of the eye are susceptible to developing fibrosis, blinding millions of people throughout the world. This disease process, regardless of the tissue type affected, is characterized by excessive extracellular matrix (ECM) production leading to scarring and loss of tissue function. There are no effective approaches to prevent, slow or reverse this disease process. The cell type responsible for causing fibrotic disease is the myofibroblast, which can result from the reprogramming of many distinct cell types including fibroblasts, pericytes, and epithelial cells that have undergone a mesenchymal transition (EMT). Understanding how these cells acquire an altered phenotype to become a myofibroblast responsible for scarring associated with fibrotic disease is key to developing anti-fibrotic therapeutics.

Cell reprogramming to a myofibroblast phenotype is triggered by specific transcription factors (TFs) that induce changes in cell phenotype. However, we do not understand how these reprogramming changes are induced at the molecular level. Lineage-specific TFs overcome the barrier of condensed arrays of nucleosomes that are associated with repressed genes which have to be activated during cell reprogramming. Therefore, reprogramming events must involve changes in epigenetic markings of chromatin, such as covalent modifications of histones by histone modifying enzymes, which results in alteration of chromatin structure and thereby facilitate binding of TFs and impact gene transcriptional programs. These issues are of general biological significance to fibrotic diseases throughout the body, as they merge several key phenomena, transcription, epigenetics, chromatin structure and cell reprogramming.

While there is data to suggest that the fibrotic process is under epigenetic control, we are only in the infancy of understanding this emerging field. Studies on this topic so far show a role for DNA methylation in regulating fibrosis, with little understanding to date about the role of histone modifications. Herein, we describe mechanisms of action and therapeutic treatments and methods for modifying epigenetic and transcriptional mechanisms that are utilized during very early stages of reprogramming for induction of fibrotic disease. Accordingly, for any number of fibrotic diseases, we teach therapeutics and methods that can be utilized to alter the process of differentiation of myofibroblasts to prevent or reduce the formation of fibrosis.

As known to those of ordinary skill in the art, DNA is wrapped around nucleosomes (chromatin structures composed of several histone proteins) which allow DNA to maintain its compact structure and regulate gene activity. The maintenance of nucleosome arrays, and therefore chromatin structure, is provided by so-called epigenetic mechanisms during different stages of the cell cycle. Cell differentiation also relies on epigenetic mechanisms, although the exact way that changing chromatin structure and gene activity impacts differentiation is poorly understood. The phenotypic outcome of cell reprogramming to a myofibroblast, the major cell type associated with fibrosis and fibrotic disease progression is altered by targeting epigenetic mechanisms.

Herein, we show that reprogramming of cells normally tasked with repair to a myofibroblast phenotype requires transient de-condensation of chromatin/nucleosome structure during early stages of DNA replication. This "opening" of the chromatin exposes regulatory sequences in the DNA of repressed genes and facilitates binding of lineage-specifying transcription factors (TFs) to DNA. Tri-methylated lysine 27 of Histone 3 (H3K27me3) is a key epigenetic mark associated with the most condensed ('closed') chromatin structure. Importantly, H3K27me3 marks all repressed genes in the genome, among which are genes that have to be activated to change transcriptional programs during cell differentiation.

Histone modifying enzymes for lysine 27 of histone H3 (H3K27) include two groups of enzymes with antagonistic activities: 1) H3K27 methyltransferases (HMT) EZH1 and EZH2 that catalyze the addition of methyl groups to H3K27, and 2) H3K27me3 de-methylases (KDM) UTX and JMJD3, involved in catalyzing the removal of methyl groups from H3K27me3. Thus, targeting of KDM enzymes with small molecule inhibitors leads to an increase of H3K27me3, and as a result to a more closed, condensed structure of chromatin (rapid accumulation of H3K27me3) on newly replicated DNA. This condensed structure of chromatin blocks binding of TFs essential for reprograming to myofibroblasts and will prevent or slow fibrosis.

Therefore, the presence of H3K27me3 in the genome strongly correlates with the condensed structure of nucleosomes. Accordingly, H3K27me3 provides for a reliable readout of chromatin compaction. We have shown that inhibitors of enzymes responsible for de-methylating of H3K27, which allow for faster accumulation of H3K27me3 and a closed chromatin structure would block the ability of pro-fibrotic TFs to bind to the DNA and the development of fibrosis.

Accordingly, herein, we describe therapeutic treatments for preventing or reducing the formation of fibrosis. These treatments include use of particular H3K27me3-specific KDMs blocking agents, and methods of use of the same in procedures to prevent the formation of, or reduce the formation of fibrosis. Accordingly, broadly, the embodiments of the present disclosure relate to compositions and methods to generate effective epigenetic-based therapeutic approaches to slow or prevent fibrotic disease. Further embodiments are directed towards compositions and methods to prevent the myofibroblast phenotype expression with fibrosis-promoting extracellular matrix proteins and fibrotic disease progression.

The therapeutic treatments described herein are effective in preventing fibrosis in situations in which we can access an injury or dysmorphogenic tissue before the fibrotic process becomes established in the tissue. Fibrosis is a widespread issue, whether related to the excess formation of scar tissues, which has created an entire line of medicine related to plastic surgery—or reduction of fibrosis formation.

Indeed, fibrosis formation is problematic in pulmonary fibrosis, cystic fibrosis, cirrhosis, atrial fibrosis, endomyocardial fibrosis, glial scarring, arterial stiffening, arthrofibrosis, crohn's disease, keloids, myelofibrosis, systemic fibrosis, etc. Fibrosis simply covers every organ and skin type of the body. Many of these diseases are slow progressing, and treatment may be suitable herein, to reduce the formation of fibrosis or slow disease progression.

However, certain acute fibrotic events are also of interest, for example, scarring due to surgical procedures. Formation of fibrosis in these instances can be reduced or eliminated, and thus prevent such tissue injury or, for many, the mental components that go with the formation of fibrotic tissue. One area that may be targeted are injury/surgery/disease in the visual system including the lens post-cataract surgery, fibrotic disease, Posterior Capsule Opacification (PCO), hazing/opacification of the cornea following cornea injury/surgery including Lasik, age-related macular degeneration (AMD), scarring following surgery of all types, scarring following skin injury.

For example, in a PCO model, using an ex vivo lens mock cataract surgery model in chick embryos that recapitulates features of PCO, we investigated the cell reprogramming events involved in regulating changes in epigenetic markings of chromatin, which result in alterations of chromatin structure and impact gene transcriptional programs to control the emergence of myofibroblasts. Before surgery and until the first day following induction of cell reprogramming, we found that chromatin is characterized by a significant delay in the accumulation of the key repressive histone mark H3K27me3 on the myofibroblast progenitors following DNA replication. This signifies an "open' nascent chromatin structure, revealing a potential window of opportunity for the recruitment of pro-fibrotic TFs, such as MRTF-A, to DNA that are required for the reprogramming of the progenitor cells to a myofibroblast.

Following this H3K27me3 rapidly accumulated on nascent DNA after replication, consistent with 'closed' nascent chromatin, reflective of a tight structure of chromatin that would prevent association of unwanted TFs to DNA to maintain the newly acquired differentiated fibrotic phenotype. Changes in the rate of accumulation of H3K27me3 methylation associated with the development of fibrosis can be regulated by H3K27 modifying enzymes, which include the H3K27 tri-methylase EZH2 and H3K27 demethylase UTX.

Using newly developed experimental paradigms as described herein, we found that epigenetic marking during cell proliferation relies not on the transfer of modified histones to daughter strands, but rather on stable association of multiple histone-modifying proteins during DNA replication. Similar results were obtained in multiple lens models of cell reprogramming leading to fibrotic disease. Lens cells before injury and until the first day following surgery in the ex vivo chick model have chromatin that is characterized by a significant delay in the accumulation of the key repressive histone mark H3K27me3 following DNA replication. This signifies a de-condensed structure of nucleosomes.

The same 'open' post-replicative chromatin was also discovered in mouse and human lens cells during their induction to the myofibroblast phenotype, suggesting that this is a previously unknown pivotal property of all myofibroblast progenitor cells. Accordingly, our data not only supports the therapeutic treatments in animal models, but translates through to human cells. Our data confirms that this 'open' state of post-replicative chromatin is more amenable to binding of newly induced specific transcription factors (TFs) essential for cell reprogramming. Importantly, the state of 'open' chromatin may be manipulated in order to change the ability of TFs to associate with their target sites on DNA to therapeutically target myofibroblast differentiation.

Fibrosis, while impacting nearly every tissue in the body, has a particular impact on and affects most tissues of the eye, leading to blindness in millions of people worldwide. Few options exist to treat the scarring associated with this pathological disease process. The key cellular mediator of fibrosis is the myofibroblast characterized by its α-smooth muscle actin (αSMA)-mediated contractile function and synthesis of an altered extracellular matrix environment.

We focused on understanding how a cell type is reprogrammed to acquire a new transcriptional profile that induces the cell to become a fibrotic disease-causing myofibroblast in order to develop therapeutic tools to treat fibrotic disease. While studies to date have focused on the growth factors and receptors that signal the transition to a myofibroblast phenotype, few studies have addressed the epigenetic mechanisms that underlie this phenotypic change. Epigenetic regulation is thought to be essential to the differentiation of other cell types, including stem cells. While we know the end result of epigenetic changes during cell differentiation, the mechanistic aspects of epigenetic inheritance that change a cell's phenotype during differentiation still remain a mystery. This lack of knowledge is mostly due to the absence of experimental approaches for investigating chromatin structure during DNA replication the disruptive cell cycle stage during which chromatin is remodeled.

We developed methods that allow, for the first time, examination of the nature of epigenetic marking of chromatin and the re-assembly of proteins on DNA during replication. Herein, we describe experimental approaches regarding epigenetic mechanisms regulating myofibroblast differentiation and the preservation of the myofibroblast phenotype which results in tissue scarring. For these studies we used an ex vivo mock cataract surgery model of the lens fibrotic disease, Posterior Capsule Opacification (PCO), as well as human lens culture models in which epithelial mesenchymal transition (EMT) leading to fibrosis is induced by exposure to TGFβ. Using these model systems we studied the epigenetic cell reprogramming to a fibrotic disease causing myofibroblast on a single cell level, as well as tested anti-fibrotic therapeutics. Because of the conservation of myofibroblast differentiation, therapeutic strategies described herein will generate a consistent effect for modifying myofibroblast differentiation regardless of the cellular source or tissue type, therefore our findings have wide application for the treatment of fibrosis in many tissues.

Methods and Examples

FIG. 1 describes the manipulation of chromatin structure using epigenetic inhibitors to block pro-fibrotic transcription factors from associating with DNA to prevent the onset and progression of fibrotic diseases. FIG. 1 (top) depicts an "open" chromatin structure, wherein the structure is able to be bound by transcription factors, which can, in some cases re-program cells to a myofibroblast fate leading to fibrotic disease. Instead, by blocking the enzymatic activities of the H3K27me3 de-methylases UTX/JMJD3 with a therapeutic, in this case GSK-J4, the structure of the chromatin becomes 'closed' and prevents binding of pro-fibrotic transcriptions factors, such as MRTF-A. Subsequently, cell reprogramming to a myofibroblast phenotype and changes in the ECM environment associated with onset and progression of fibrotic disease are prevented.

We tested this epigenetic targeting strategy using a clinically relevant ex vivo chick mock cataract surgery model that recapitulates the major features of the lens fibrotic disease, PCO, as well as a human lens cells (SRA01/04). Human SRA01/04 lens cells are studied extensively for the acquisition of a mesenchymal phenotype resulting from an Epithelial Mesenchymal Transition (EMT) after exposure to TGFβ associated with the development of lens fibrosis [4, 5]. In studies with the SRA01/04 human cell line we now show that TGFβ induces expression of FN-EDA and collagen I, both components of a fibrotic-promoting ECM environment. Importantly, we found that the epigenetic paradigm for myofibroblast emergence that we discovered in our studies with the ex vivo mock cataract surgery cultures is replicated in these lens cell upon treatment with TGFβ.

Figure 2A:
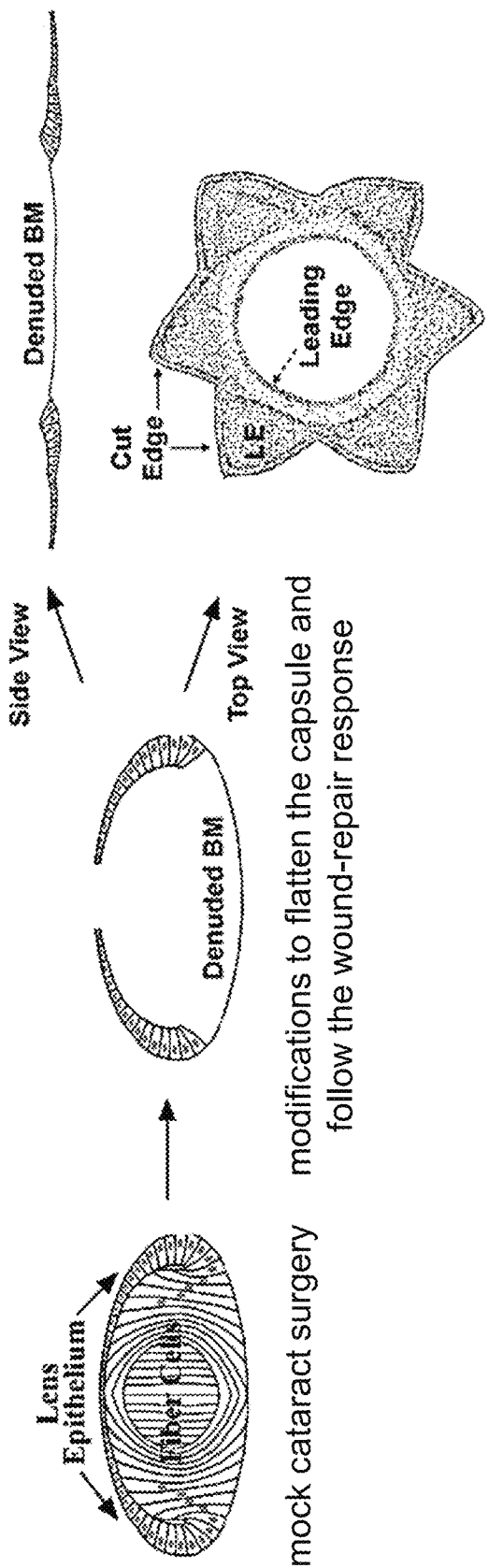
FIGS. 2A-2C illustrate ex vivo mock cataract surgery wound repair/fibrosis model and the process of wound healing, which is completed by day 3, as shown in 2C.

FIG. 2A illustrates how the ex vivo mock cataract surgery explants are created. Ex vivo mock cataract surgery explants provide a powerful model in which to study wound healing as well as the development of fibrotic disease. Briefly, to create this model, the fiber cell mass is hydroeluted from the lens leaving behind lens epithelial cells that remain adherent to the lens capsule. The resultant ex vivo explant when placed in culture is star shaped, with the adherent cells located in the points of the star. In response to the injury induced by the surgery, mesenchymal cells involved in repair move to the wound edges.

Figure 2B:
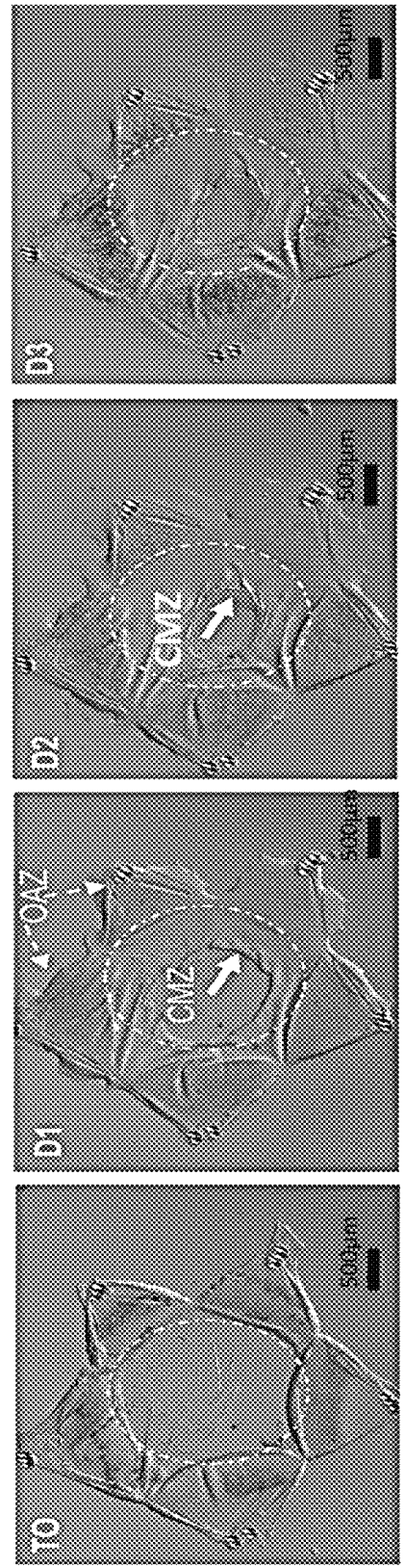
Figure 2C:
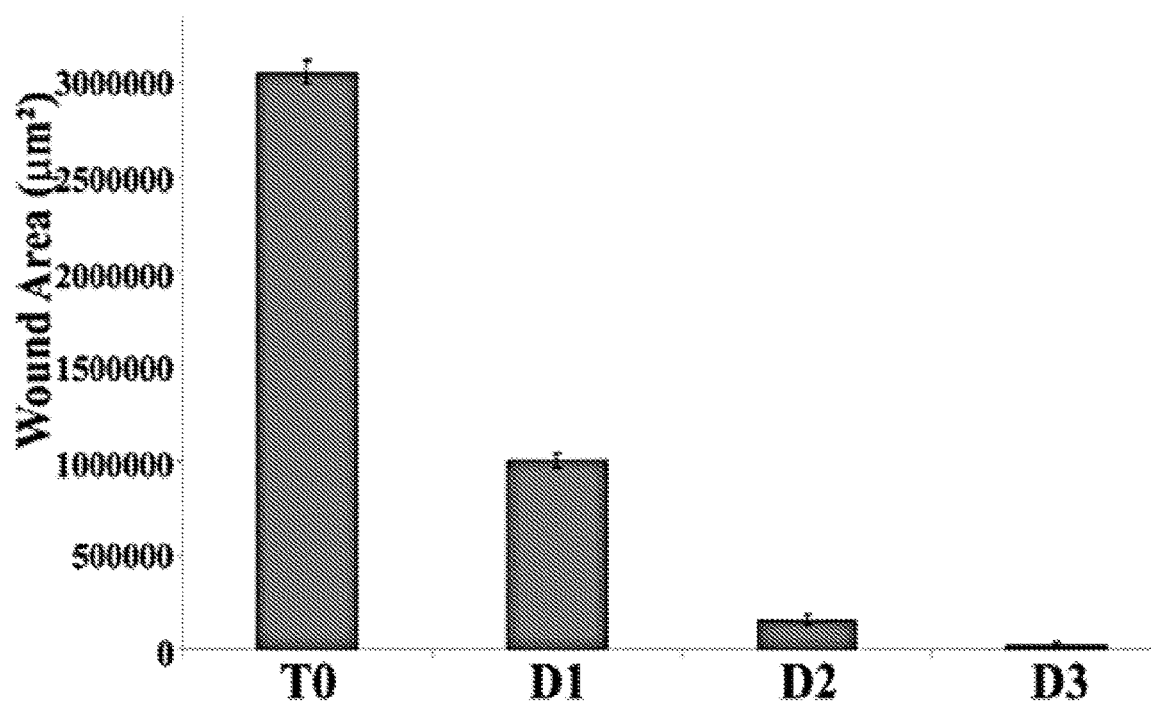
Figure 3A:
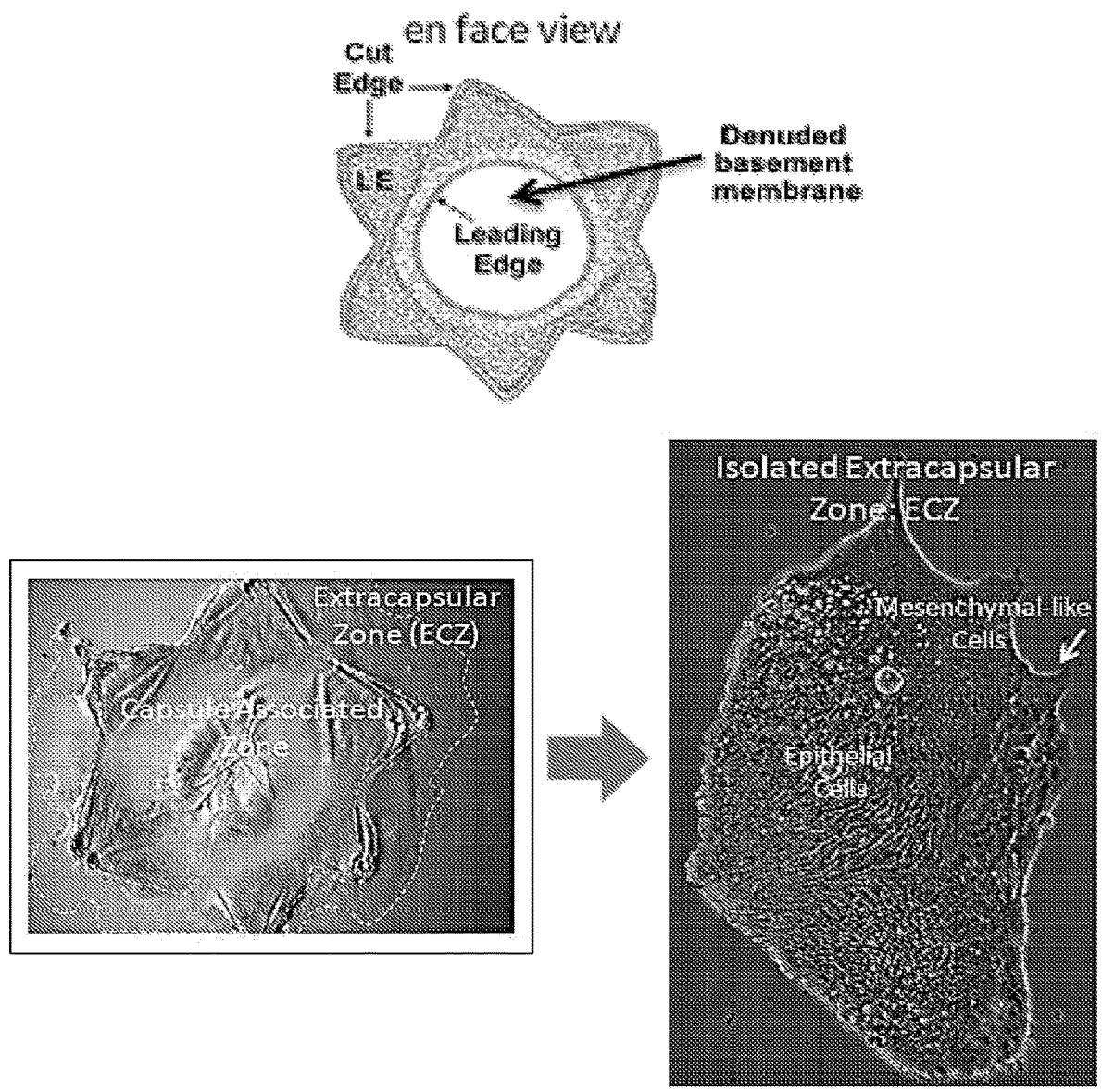
FIGS. 3A and 3B illustrate cells migrating from ex vivo explant onto the rigid tissue culture substrate called the ECZ provides an ideal model to study mechanism of myofibroblast emergence and shows that CD44+ leader cells that serve as the myofibroblast progenitors are highly proliferative
Figure 3B:
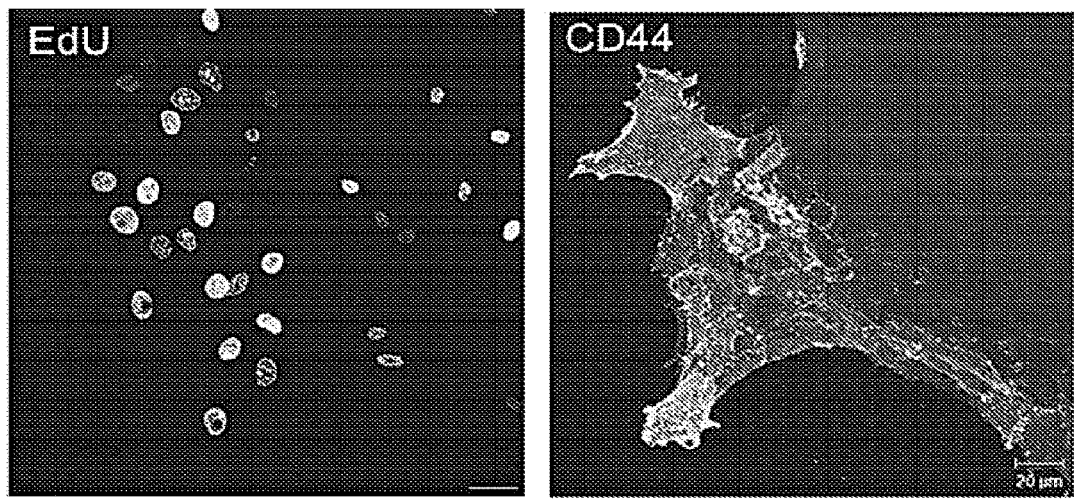
Figure 4:
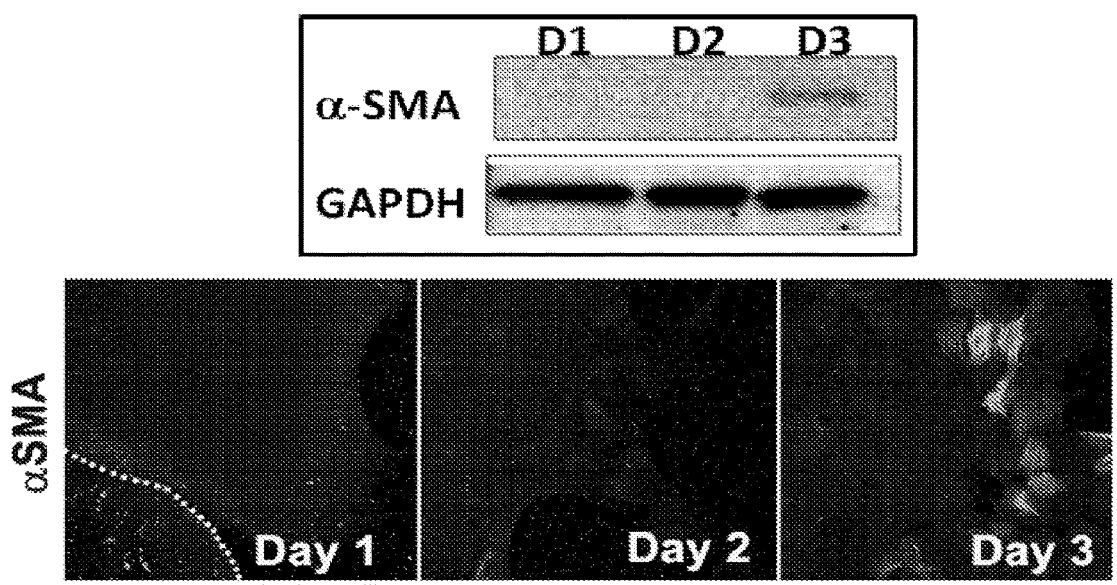
FIG. 4 shows that αSMA positive myofibroblasts emerge at the leading edge of the ECZ by day 3.

As shown in FIG. 2B wound healing across the denuded basement membrane is typically completed by day 3. Lens epithelial cells led by a leader cell population, which expresses the surface receptor CD44+ [42], move collectively to repopulate the denuded area of the wounded lens capsule (where the differentiated lens fiber cells were removed). FIG. 2C depicts the wound area over a three-day period. In FIGS. 3A and B CD44+ leader cell population that has migrated to the outside wound edge of the explants (FIG. 3A, left panel, right arrow) directs the collective migration of lens epithelial cells onto the rigid tissue culture substrate, a region we refer to as the extracapsular zone (ECZ). FIG. 3B shows the CD44-rich highly proliferative population at the leading edge of lens epithelial cells migrating across the tissue culture plastic. FIG. 4 demonstrates that αSMA+ myofibroblasts first appear at the leading edge of the ECZ on day 3, preceded by the assembly of a fibronectin EDA (FN-EDA) matrix environment at day 2, an ECM shown to be a key fibrosis-inducing factor. Therefore, within one model system we can assess epigenetic targeting strategies for preventing fibrosis and determine how these approaches will affect normal wound healing. This ex vivo model was used to investigate the epigenetic mechanisms (detailed below) involved in regulating cell reprogramming to a myofibroblast phenotype associated with lens fibrotic disease.

Figure 5:
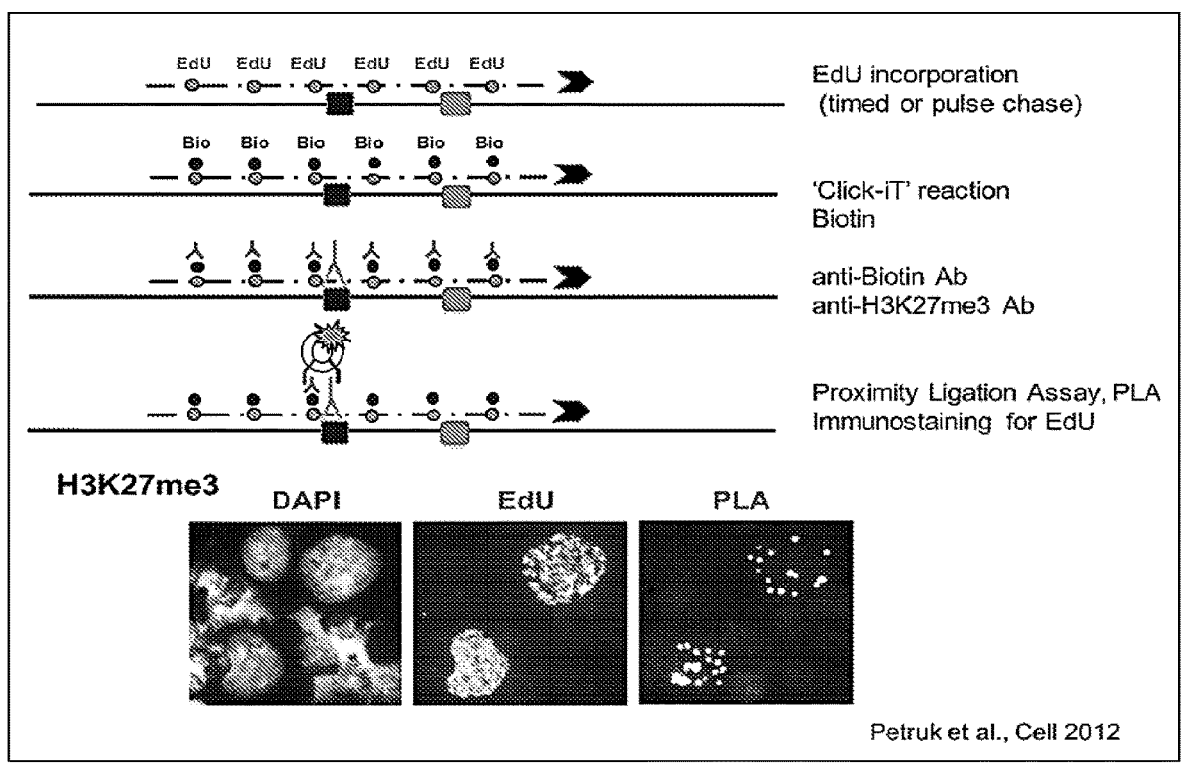
FIG. 5 illustrates a schematic diagram of the Chromatin Assembly Assay (CAA), which reveals how chromatin structure is re-established following DNA replication.

To study the epigenetic mechanisms associated with cell reprogramming to a myofibroblast phenotype we are using a state of the art assay called the Chromatin Assembly Assay (CAA). FIG. 5 is a schematic diagram of the CAA used to reveal how chromatin structure is re-established following DNA replication. Briefly, DNA is labeled in vivo in a pulse-chase manner with EdU, which is then chemically conjugated with biotin using a 'Click-iT' reaction. The proximity of a protein of interest to nascent DNA is then examined by Proximity Ligation Assay (PLA, Olink, Bioscience). In PLA, both chromatin-associated protein and biotin labeled DNA are detected with primary antibodies and then with secondary antibodies that are conjugated with short strands of DNA. Addition of complementary linker oligonucleotides allows formation of a DNA circle if antibodies are within approximately 40 nm of each other. DNA circles are then amplified by rolling circle amplification (RCA), fluorescently labeled oligonucleotides are added that will hybridize to the RCA product to generate a fluorescent signal. PLA is a powerful single cell technique that detects single molecule interactions with high sensitivity ($10^{-40}$ M) and specificity. Cells can be then immunostained with any additional antibody to examine the specificity of interactions (e.g. specific PLA signals are detected only in EdU-labeled cells), and to assess tissue specificity using different protein markers. Reliable pulse-chase EdU labeling in cells can be detected from 3-5 min to several hours. CAA is a rapid and convenient method to examine the kinetics of assembly of proteins and histones on daughter DNA after replication at a single cell level. PLA appears as punctuate dots within EdU labeled nuclei. The example shows accumulation of H3K27me3, a mark of closed chromatin, accumulating on nascent DNA. In the example shown in FIG. 5 (bottom) the chromatin is closed.

Figure 6:
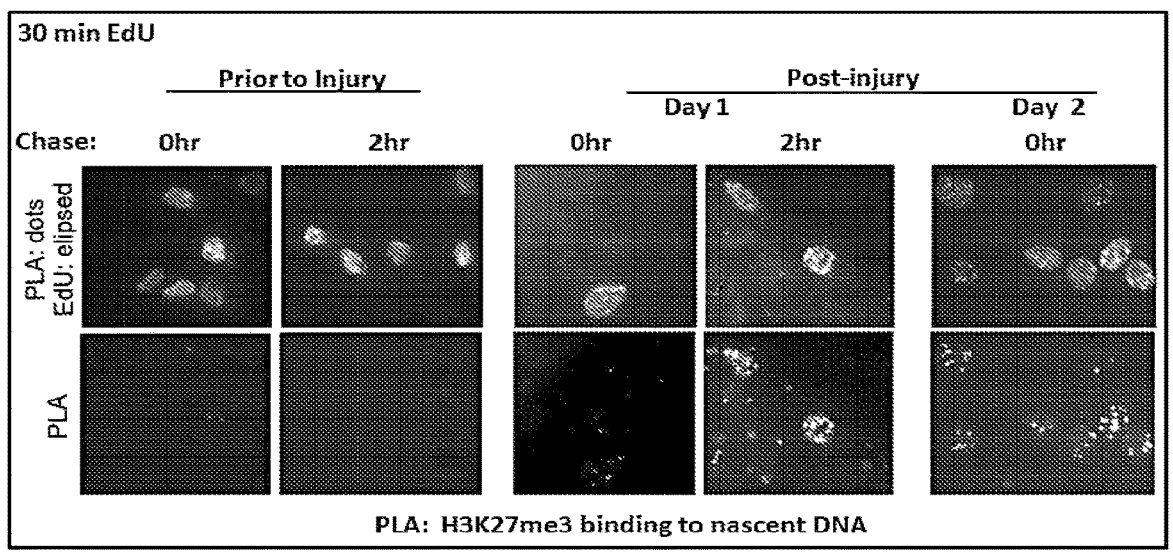
FIG. 6 shows the period of period of 'open' post-explicative chromatin in the ex vivo mock cataract surgery cultures, revealing the time period of cell reprogramming to a myofibroblast phenotype.

FIG. 6 defines the period of 'open' post-explicative chromatin in the ex vivo mock cataract surgery model using CAA. Using the ex vivo model we first wanted to determine when nascent chromatin is 'open' to indicate the time period in which cell reprogramming to a myofibroblast may be occurring. The results indicate that the induction of myofibroblast differentiation is accompanied by a several hours delay in accumulation of H3K27me3 to nascent DNA. Thus, indicating a period of time between day 1 and day 2, when cell reprogramming to a myofibroblast is occurring. Lens epithelial cells prior to injury and cells in the ECZ region 1 and 2 days after surgery were labeled with EdU for 30 min, followed by 2 hour chase. CAA was performed for H3K27me3, followed by immunostaining for biotin (EdU).

PLA signals only (dots) are shown in lower panels. In contrast, on day 2 after injury, H3K27me3 accumulates rapidly, indicating that by day 2 nascent chromatin is closed.

Figure 7A:
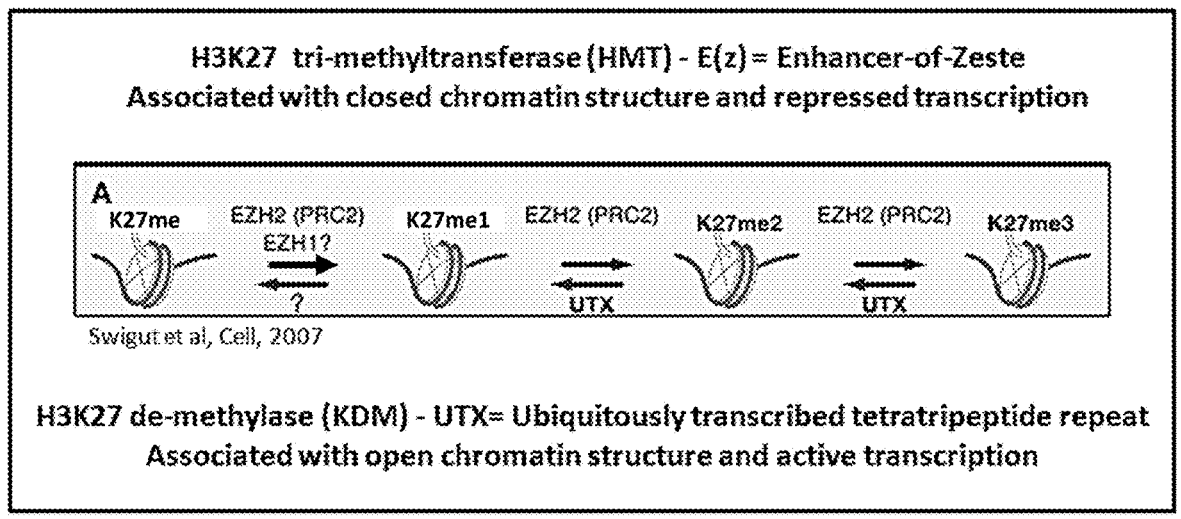
FIGS. 7A-7C illustrate a diagram of the H3K27 modifying enzymes, immunolocalization studies for EZH2 and H3K27me3 in the ECZ, and CAA showing that EZH2 accumulation on day 2 in the ECZ.
Figure 7B:
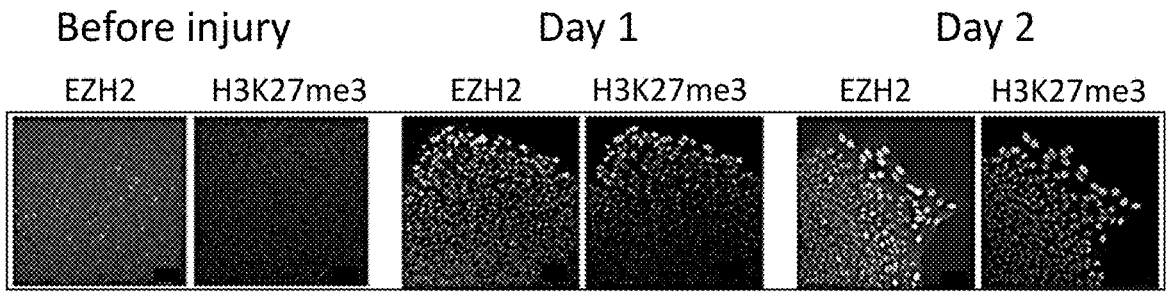
Figure 7C:
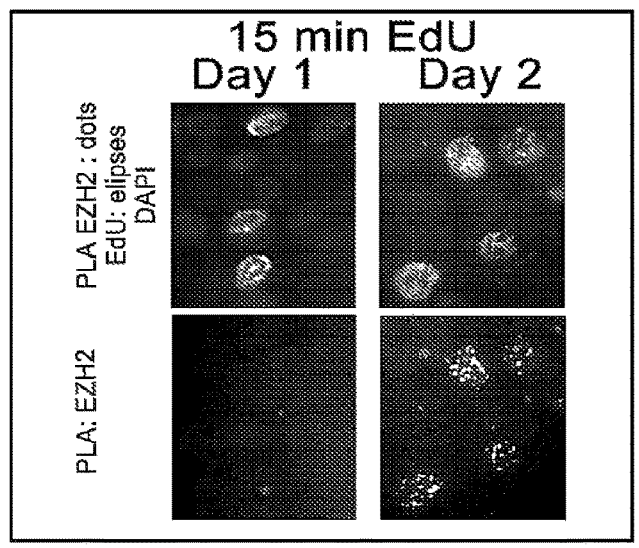

FIG. 7 illustrates the major H3K27 modifying histone enzymes: Histone methyltransferase EZH2, which adds methyl groups to H3K27 and the histone de-methylase UTX, which removes methyl groups from H3K27. Manipulating activity of these enzymes is a major way to modify H3K27, and to change chromatin structure. FIG. 7B shows co-immunostaining of H3K27me3 and the H3K27 tri-methyltransferase EZH2 in lens cells from the ECZ region of the ex vivo cataract surgery explant model before and after injury. EZH2 expression increased in leader cells coincident with the increase in H3K27me3 post injury. FIG. 7C shows the association of EZH2 on labeled nascent DNA in the ECZ region of the lens 1 day and 2 days after mock cataract surgery. CAA was performed for EZH2 and for biotin (EdU). PLA (dots) are shown in lower panel. On day 2 EZH2 rapidly accumulates on nascent DNA coincident when we observed the accumulation of H3K27me3. Thus, we have defined an open period of chromatin (absence of H3K27me3 and EZH2 accumulation) on day 1 to day 2, when reprogramming to a myofibroblast can occur. By day 2, we have established that chromatin is closed, and that no new transcriptional program can potentially be acquired.

Figure 8:
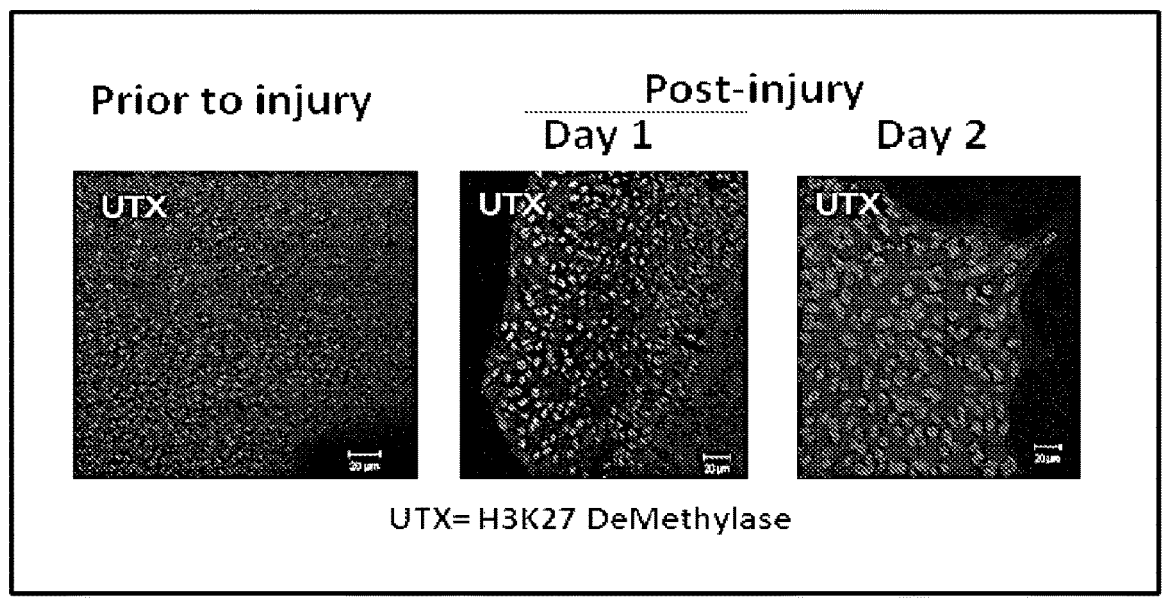
FIG. 8 illustrates that UTX expression is increased in response to injury in the ex vivo mock cataract surgery cultures.

FIG. 8 shows that expression of the H3K27 de-methylase UTX is increased in response to injury. Therefore, the H3K27 demethylase, UTX is poised to prevent methylation of H3K27 on day 1, to keep chromatin in the open state. Thus, manipulation of demethylase activity represents a key epigenetic strategy to induce closure of chromatin to prevent the adoption of new transcription program associated with the onset of fibrotic disease. We tested this below in FIGS. 10-13.

Figure 9A:
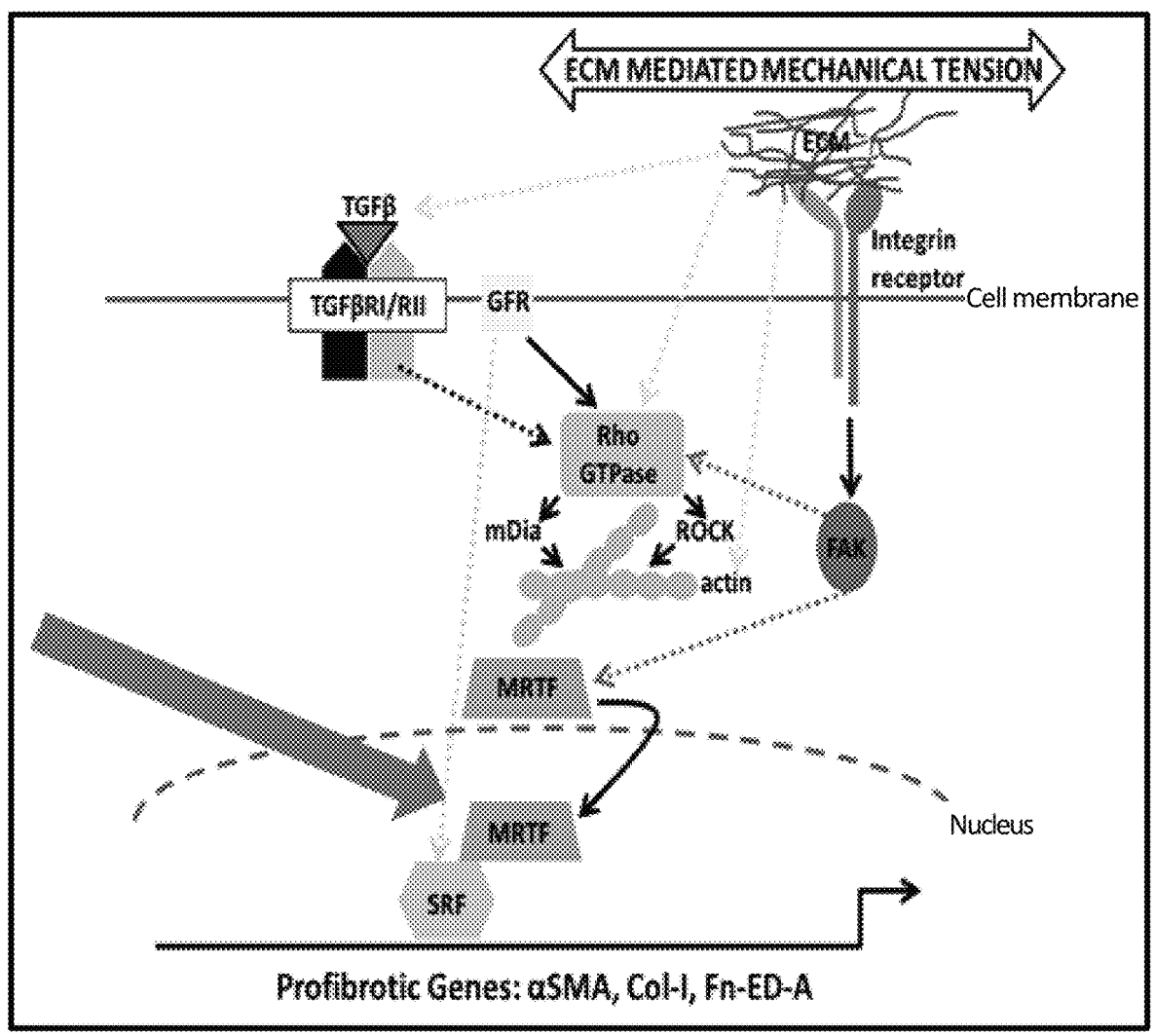
FIGS. 9A-9C illustrate how the pro-fibrotic transcription factor MRTF-A is activated and 9B depicts that MRTF-A recruitment to DNA occurs during DNA replication, while 9C depicts a thymidine block.
Figure 9B:
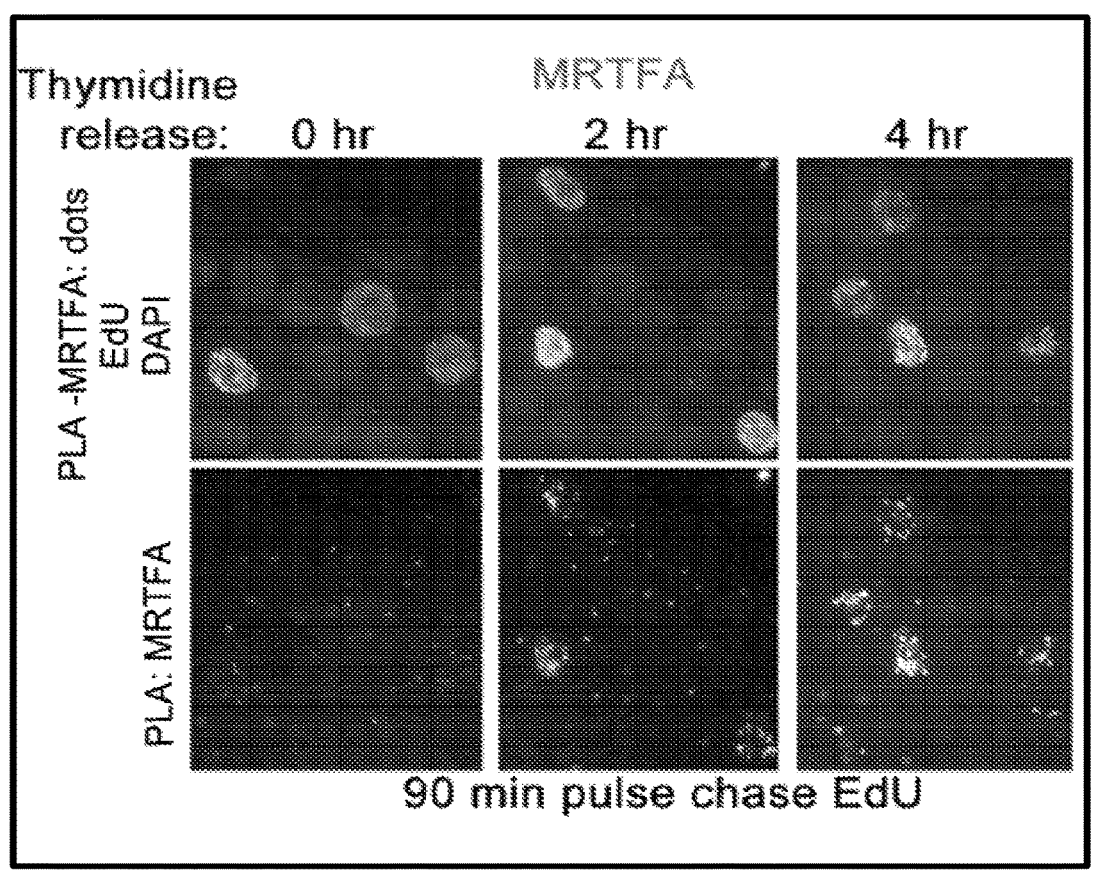
Figure 9C:
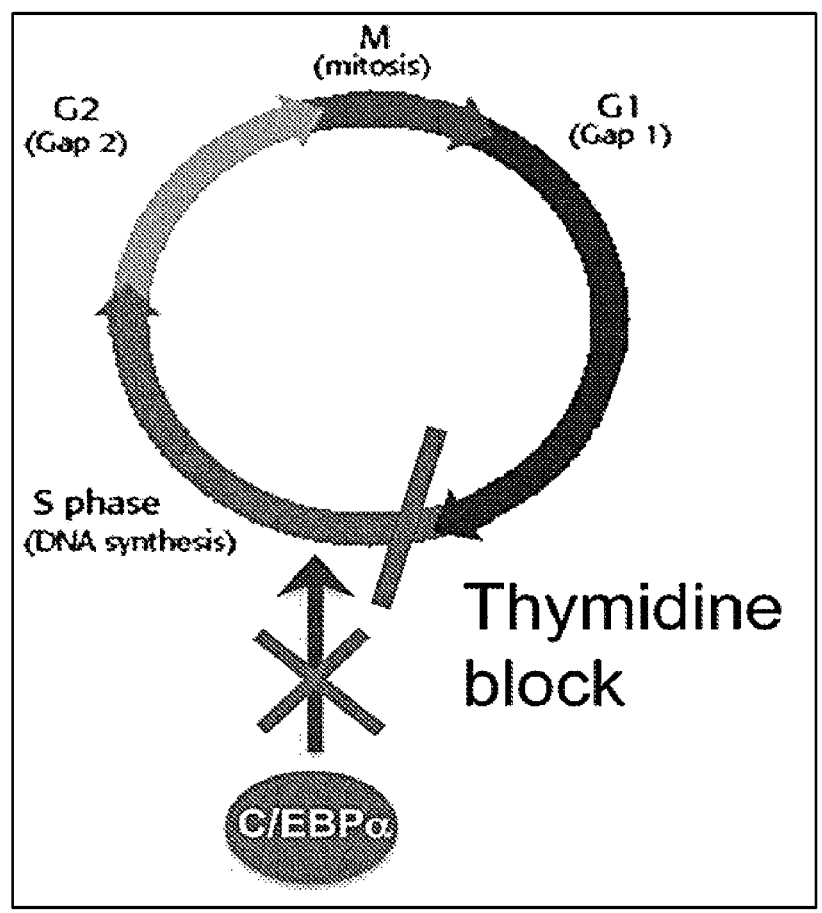

FIG. 9A depicts a model of activation of MRTF-A downstream of the TGFβ and ECM mediated mechanical signaling, leading to induction of pro-fibrotic genes. FIG. 9B shows MRTF-A recruitment to nascent DNA occurring only during DNA replication. One day after surgery, cells of the ECZ region were labeled with EdU for 30 min, followed by 60 min chase. Cells were then incubated with thymidine for 24 hr. Thymidine was removed and cells were kept for additional 2 and 4 hr. CAA was performed for MRTF-A followed by immunostaining for biotin (EdU). The upper panel in FIG. 9B shows staining with DAPI, EdU and PLA; the lower panel shows PLA dots only. These findings indicate that recruitment of the pro-fibrotic lineage transcription factor MRTF-A occurs only during DNA replication. FIG. 9C depicts a chart of DNA synthesis and impacts of thymidine block.

Figure 10A:
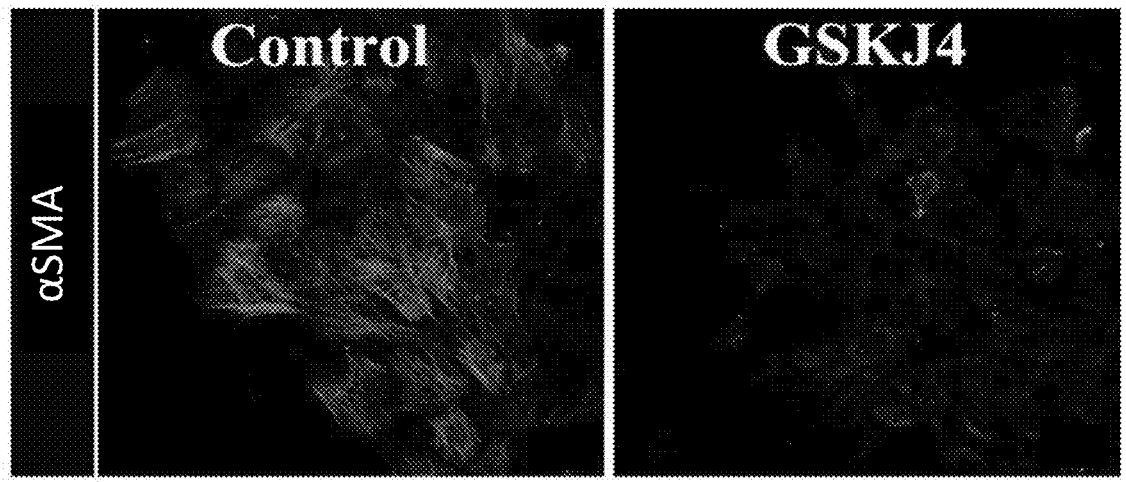
FIGS. 10A-10B show that treatment with the UTX inhibitor GSK J4 prevents α smooth muscle actin (αSMA) expression in the ex vivo mock cataract model.

Next, we tested if manipulating histone de-methylase activity could change chromatin structure to block pro-fibrotic transcription factors from binding to DNA and the acquisition to a myofibroblast phenotype associated with fibrosis. FIG. 10A shows that the selective JMJD3/UTX inhibitor, GSKJ4 effectively suppressed the emergence of myofibroblasts associated with the development of fibrotic disease. FIG. 10A, B show that treatment with GSKJ4 prevents αSMA expression in cells from the ex vivo mock cataract surgery explants. Thus, treatment with GSKJ4 prevents αSMA expression in the ex vivo mock cataract surgery model.

Figure 11:
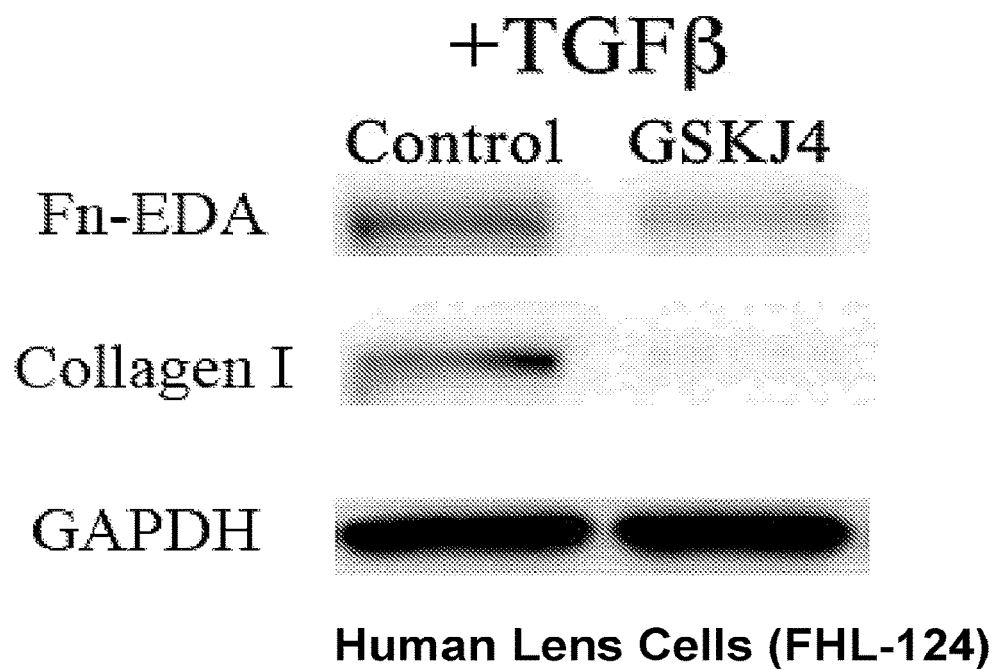
FIG. 11 shows that treatment of human lens cells (FHL 124 cell line) with GSK J4 suppresses the expression of Fibronectin EDA (FN EDA) and Collagen I, ECM molecules associated with fibrosis.

We also performed similar studies with human lens cell culture. FHL124 human lens cells, a non-transformed spontaneously generated human lens cell line from embryonic explants, were stimulated with Transforming Growth Factor β (TGFβ), a potent inducer of the fibrotic response, in the absence or presence of the UTX inhibitor GSKJ4. Western blotting was performed with antibodies to extracellular matrix molecules associated with fibrosis, including Fibronectin EDA (FN-EDA), a splice form of FN and Collagen I. FN EDA expression is tightly linked to myofibroblast differentiation and Collagen I is a defining feature of fibrosis/scarring. GAPDH was used as a loading control for WB analysis. FIG. 11 shows that treatment with the UTX inhibitor, GSKJ4 blocked TGFβ induced expression of both FN EDA and Collagen I, effectively preventing changes in ECM associated with the onset and progression of fibrosis.

Figure 10B:
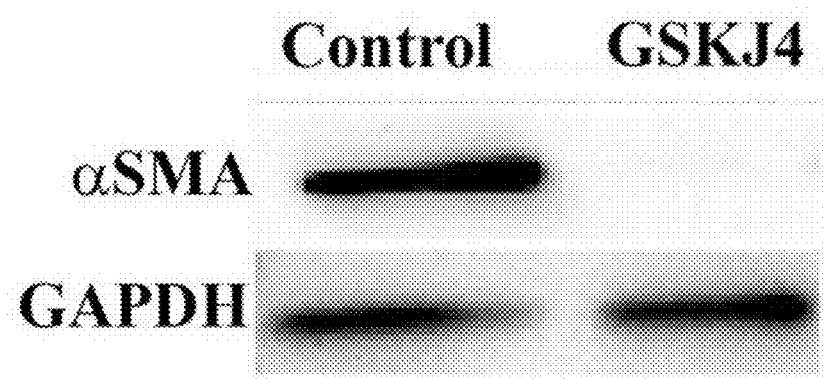

Collectively, FIGS. 10 and 11 indicate that blocking enzymatic activity of the H3K27 de-methylase UTX, leads to closed chromatin structure, and thus blocked reprogramming to a fibrotic phenotype. Accordingly, therapeutics that block the enzymatic activity of H3K27 de-methylase UTX can prevent fibrosis formation, by closing the chromatin structure and prevent the reprogramming of the myofibroblasts to a fibrotic phenotype.

Figure 12A:
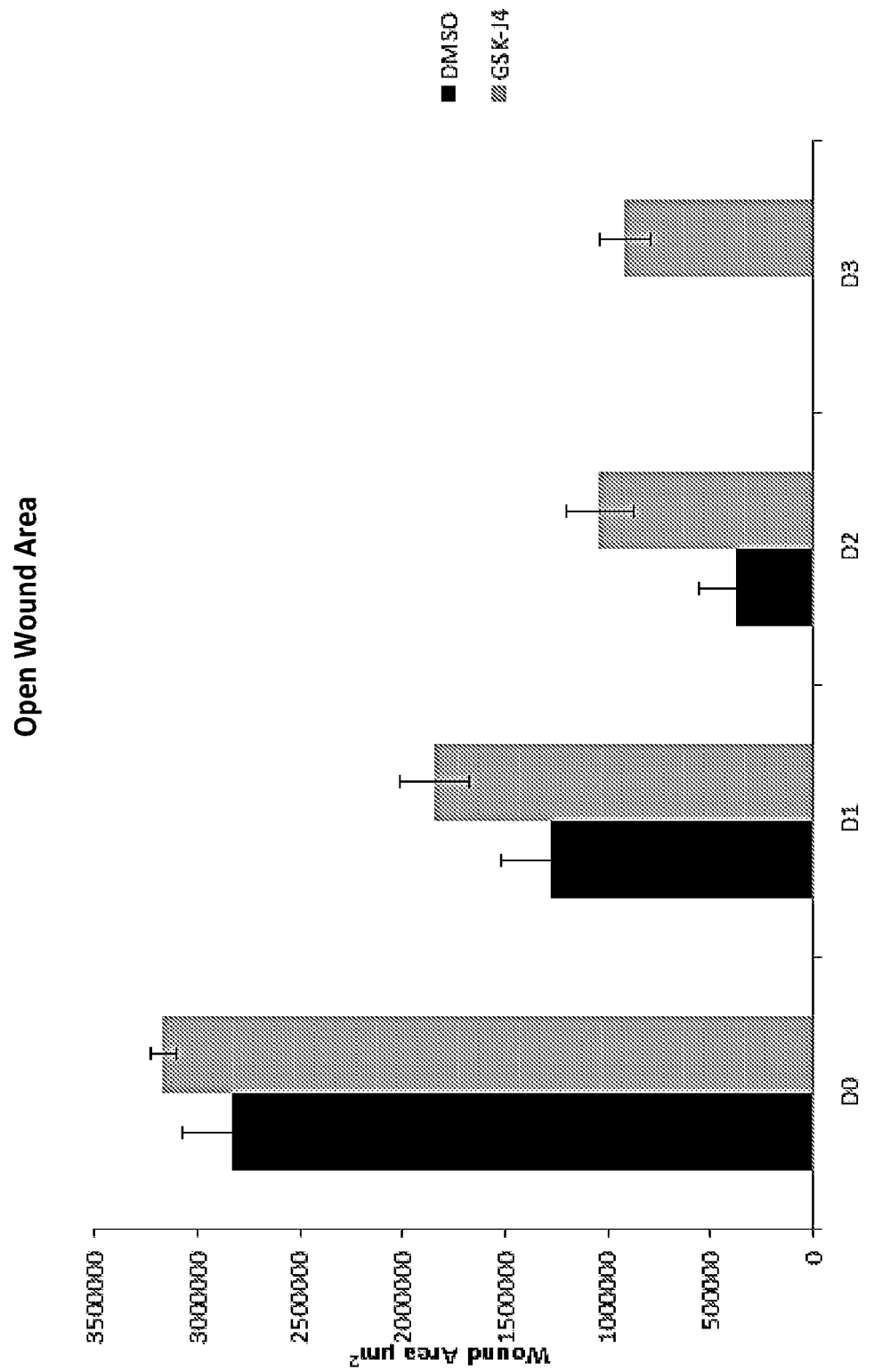
FIGS. 12A and 12B show that treatment with GSK J4 slows but does not block wound healing in the ex vivo mock cataract surgery explants over a three day period.
Figure 12B:
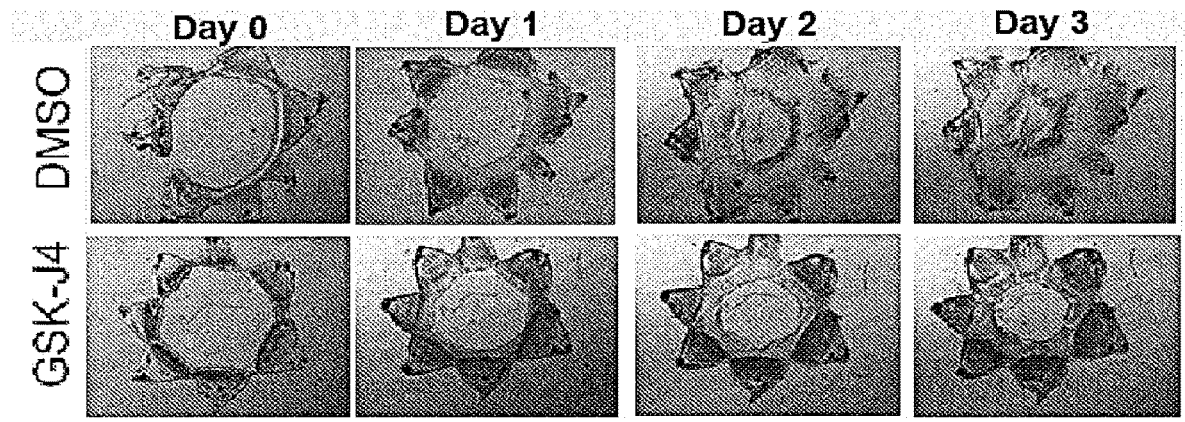

We also determined whether GSKJ4 treatment affected wound healing. It is advantageous to identify an anti-fibrotic therapeutic with limited to no effect on the normal wound healing process. FIG. 12 shows that wound healing is not prevented by treatment with the JMJD3/UTX inhibitor GSKJ4. The Ex vivo mock cataract surgery explants exposed to GSKJ4 somewhat slowed but did not prevent wound healing. Open wound area ($\mu m^2$) was measured on Day 0 (D0) through Day 3 (D3) in the presence of vehicle control (DMSO) or GSKJ4. Open wound area was measured for each ex vivo capsule D0-D3 and presented in the graph+/− SEM. Wound healing was slightly delayed by GSKJ4 treatment. Representative phase images of ex vivo mock cataract surgery explants are shown on D0-D3.

Figure 13:
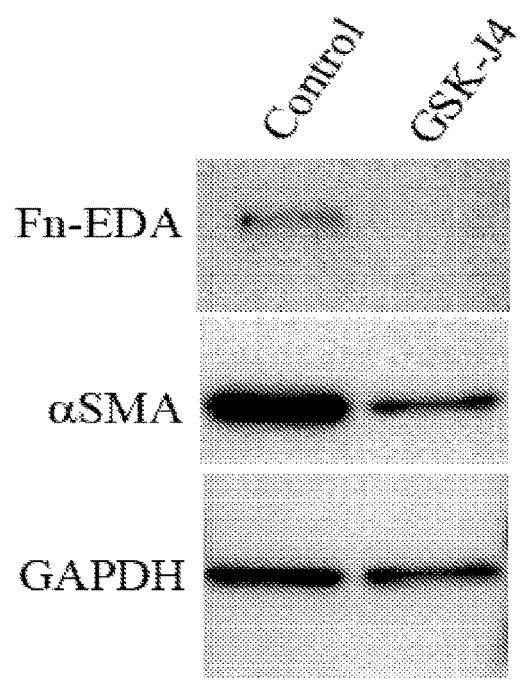
FIG. 13 shows that short-term treatment of the ex vivo mock cataract surgery explants with GSK J4 can effectively suppress Fn-EDA and αSMA expression associated with fibrosis.

Next, we tested whether a short-term treatment of GSKJ4 could be effective to block fibrosis without any effect on wound healing. FIG. 13 shows that short-term treatment with GSKJ4 was effective in suppressing expression of Fn-EDA and αSMA associated with fibrosis. Cells from the ex vivo mock cataract surgery explants were treated with vehicle or GSKJ4 for 24 hr. ECZ regions were treated 1 day after injury and inhibitor was washed away after 24 hour of treatment. We chose to add the inhibitor on day 1, during the time of open chromatin, the perfect timing to prevent cell reprogramming to a fibrotic phenotype. Lysates were collected on day 3, the time when αSMA is typically expressed, and processed for western blot analysis for expression of Fn-EDA, αSMA and GAPDH (loading control). Short-term treatment with GSK-J4 significantly inhibited αSMA and Fn-EDA expression indicating that a shorter pulse of treatment is effective for treating fibrosis.

Figure 14A:
FIGS. 14A-14C show that short-term treatment with GSK J4 can effetely suppress myofibroblast emergence without blocking wound healing in the ex vivo mock cataract surgery explants.

FIGS. 14A and B shows that short-term treatment with GSK-J4 was effective to block myofibroblast emergence without preventing wound healing from occurring. Cells from the ex vivo mock cataract surgery explant were treated for 24 hour as indicated above with vehicle or GSK-J4. Lysates were collected on day 3 and examined by western blot analysis for αSMA and GAPDH expression. The graph represents the ratio of αSMA to GAPDH+/−SEM. Treatment with the JMJD3/UTX inhibitor effectively blocked αSMA expression. In FIG. 13B we determined the effect of GSKJ4 short-term treatment on wound healing. For these studies, ex vivo cultures were treated for at the time of injury, day 0, with vehicle or GSK-J4 for a 24 hour period. Wound healing was then followed from day 0 through day 4. Phase images shown and the graph indicates open wound area+/−SEM. These data confirm that short-term treatment with GSKJ4 does not affect wound healing in response to injury in the ex vivo mock cataract surgery explants.

Figure 14B:
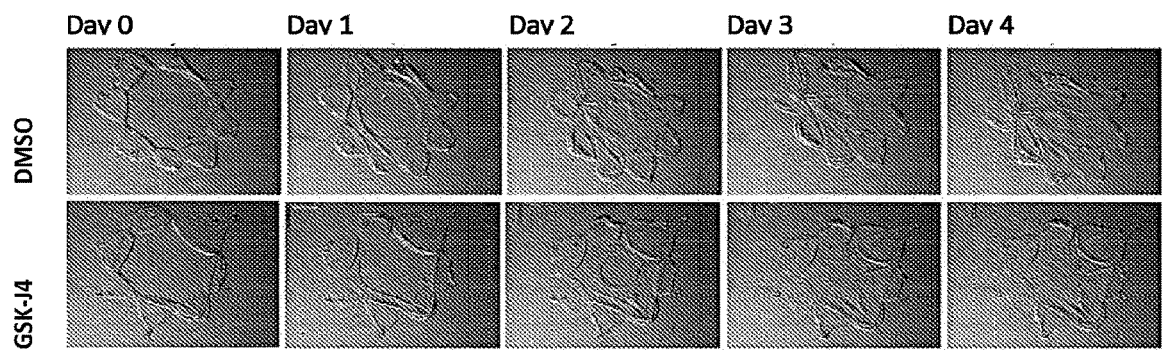
Figure 14C:
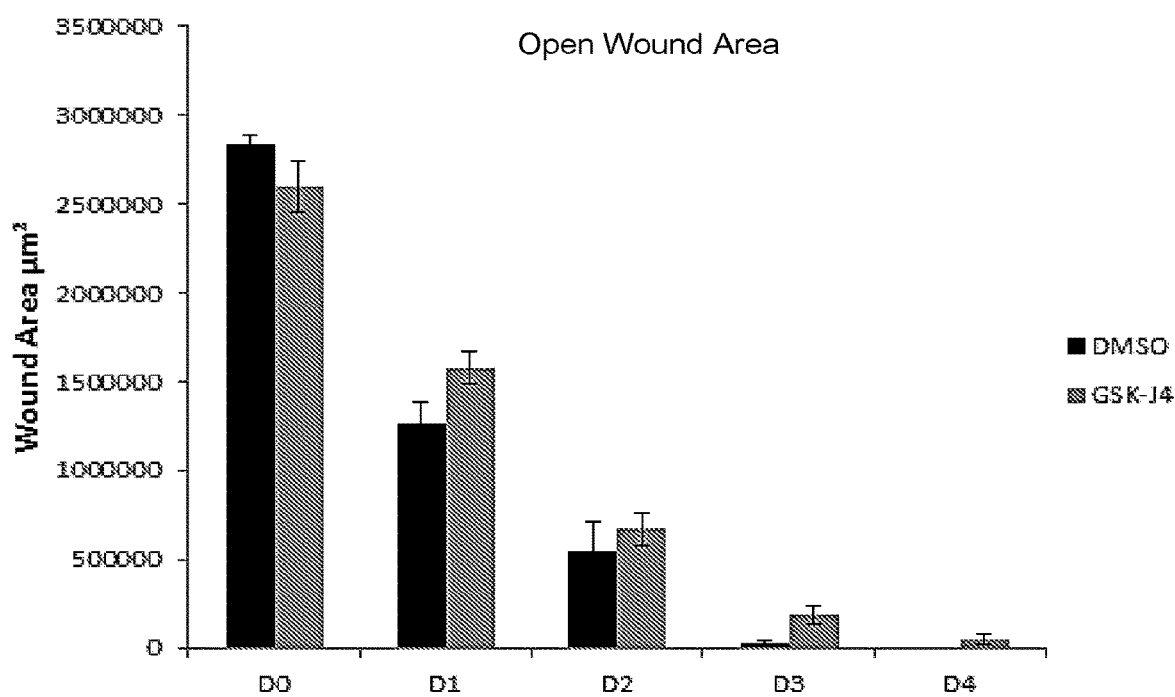

FIGS. 13 and 14 indicate that blocking enzymatic activity of the H3K27 demethylases with short-term treatment of GSKJ4 can effectively block fibrosis without affecting wound healing. These studies provide the potential for GSKJ4 treatment to be applied at the time of surgery to block fibrosis from occurring without the preventing the normal wound healing process.

Figure 15:
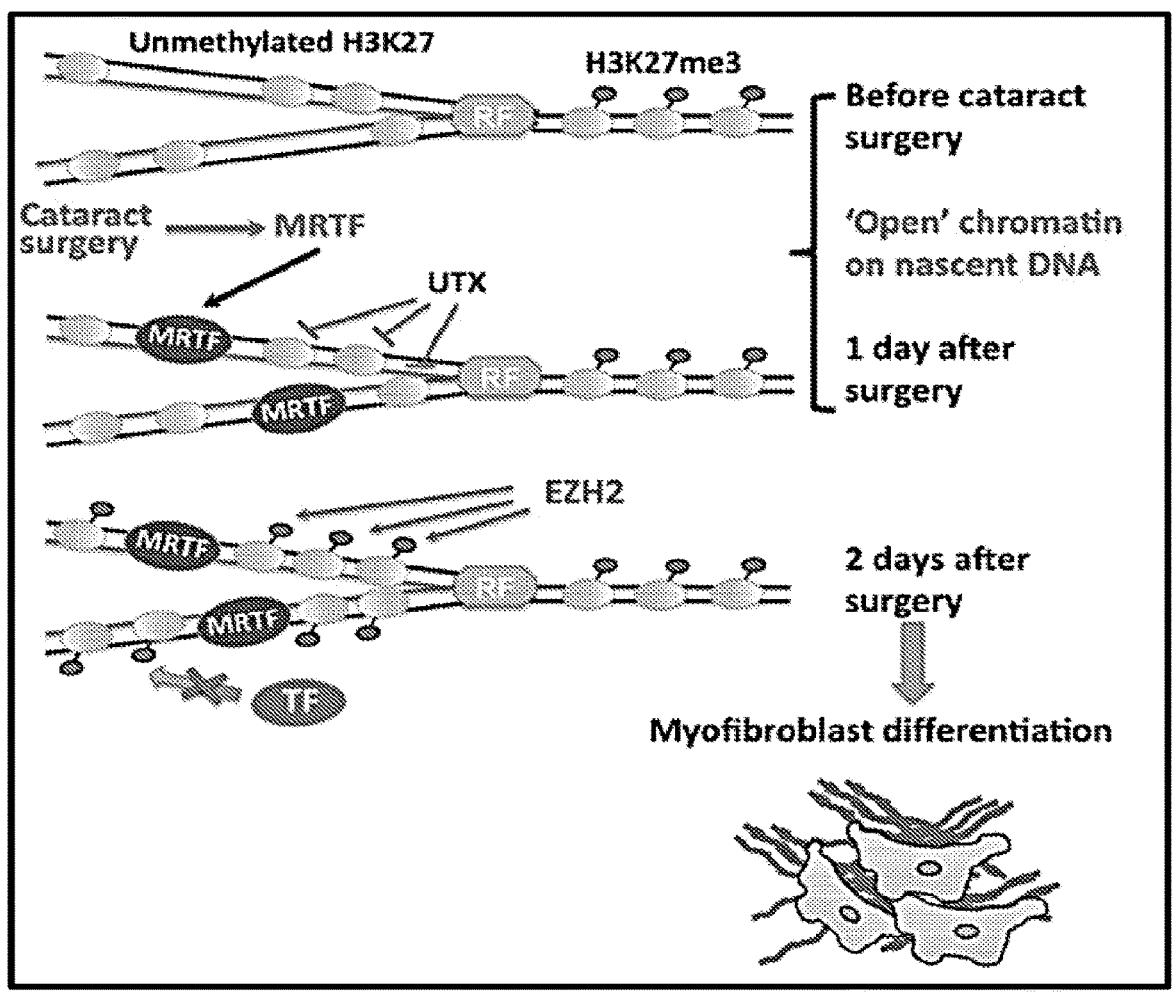
FIG. 15 illustrates changes in post-replicative chromatin that allows binding of pro-fibrotic TFs during reprogramming to a myofibroblast.

FIG. 15 presents the general model of the events that were uncovered on nascent DNA following cataract surgery. Prior to surgery, nascent chromatin is decondensed as evidenced by slow accumulation of H3K27me3 mark on DNA. This state of decondensed chromatin is maintained by the activity of the H3K27me3 KDM UTX that is induced in the region of surgery (ECZ). This open chromatin structure allows MRTF-A to bind to its sites on DNA and trigger changes in the transcriptional program leading to differentiation of progenitor cells into the myofibroblasts, hence fibrotic scarring.

Figure 16:
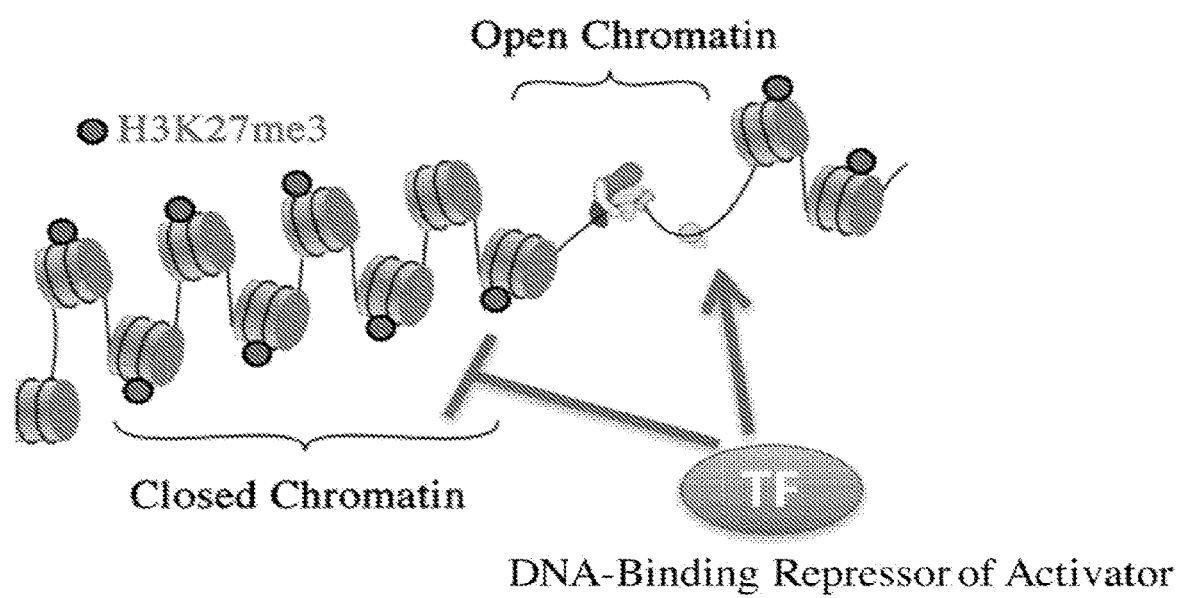
FIG. 16 illustrates how using epigenetic inhibitors to UTX/JMJD3 can manipulate chromatin structure to block reprogramming to a myofibroblast phenotype.
Figure 17:
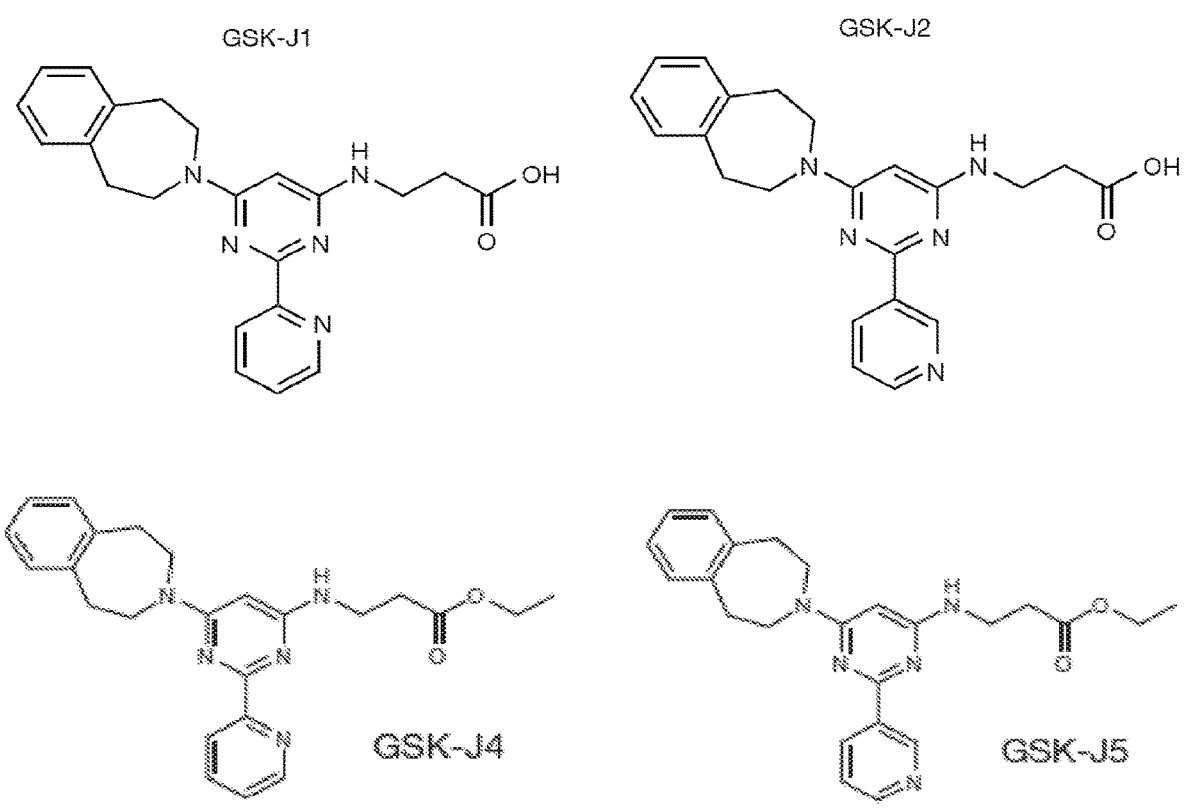
FIG. 17 depicts line structures of certain UTX/JMJD3 inhibitors including: GSK-J1, GSK-J2, GSK-J4, and GSK-J5.

FIG. 16 is a model depicting how using epigenetic inhibitors to UTX/JMJD3 can manipulate chromatin structure to block reprogramming to a myofibroblast phenotype. During myofibroblast differentiation demethylation of H3K27me3 by UTX/JMJD3 on DNA can lead to open chromatin for the transcription factor binding to induce myofibroblast differentiation. In contrast, inhibiting UTX/JMJD3 function by GSKJ4 can lead to closed chromatin structure preventing TF binding, such as MRTF-A, and blocking myofibroblast differentiation.

Therefore, the epigenetic-based therapeutic approach we describe is effective in preventing fibrosis in situations in which we can access an injury or dysmorphogenic tissue before the fibrotic process becomes established in the tissue. Good examples where such treatment would be especially effective are injury/surgery/disease in the visual system including the lens post-cataract surgery fibrotic disease Posterior Capsule Opacification (PCO), hazing/opacification of the cornea following cornea injury/surgery including Lasik, age-related macular degeneration (AMD), scarring following surgery of all types, scarring following skin injury.

Accordingly, to prevent formation of fibrosis we can: condense the chromatin, prevent reprogramming of the myofibroblasts to a fibrotic phenotype, and blocking enzymatic activity of the H3K27 de-methylase UTX. Preferably, one or more actions can be prevented through administration of a therapeutic molecule to a patient in need thereof.

Broadly, therapeutic compounds include those sufficient to inhibit JMJD3/UTX. A class of compounds sufficient to inhibit JMJD3 includes those cited in WO 2012/052390. Those of ordinary skill in the art will recognize that these molecules can be formulated into appropriate therapeutic treatments, including those suitable for injection, oral ingestion, inhalation, topical administration and the like. However, the most suitable compound is GSK-J4.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The compounds suitable as a JMJD3/UTX inhibitor may exist in solid or liquid form. In solid form, compound of the invention may exist in a continuum of solid states ranging from fully amorphous to fully crystalline. The term 'amorphous' refers to a state in which the material lacks long range order at the molecular level and, depending upon the temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compound suitable as a JMJD3/UTX inhibitor may exist in solvated and unsolvated forms. As used herein, the term "solvate" refers to a complex of variable stoichiometry formed by a solute (in this invention, a compound suitable as a JMJD3/UTX inhibitor or a salt) and a solvent. Such solvents for the purpose of the invention may not interfere with the biological activity of the solute. The skilled artisan will appreciate that pharmaceutically acceptable solvates may be formed for crystalline compounds wherein solvent molecules are incorporated into the crystalline lattice during crystallization. The incorporated solvent molecules may be water molecules or non-aqueous such as ethanol, isopropanol, DMSO, acetic acid, ethanolamine, and ethyl acetate molecules. Crystalline lattice incorporated with water molecules are typically referred to as "hydrates". Hydrates include stoichiometric hydrates as well as compositions containing variable amounts of water. The present invention includes all such solvates. The compounds suitable as a JMJD3/UTX inhibitor may have the ability to crystallize in more than one form, a characteristic, which is known as polymorphism, and it is understood that such polymorphic forms ("polymorphs") are within the scope of the invention. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered once or more than once a day. Such pharmaceutical compositions may be prepared by any of the methods well known in the pharmacy art. Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water and the like. Powders are prepared by reducing the compound to a suitable fine size and mixing with a similarly prepared pharmaceutical carrier such as an edible carbohydrate, as, for example, starch or mannitol. Flavouring, preservative, dispersing and colouring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested. Moreover, when desired or necessary, suitable binders, glidants, lubricants, sweetening agents, flavours, disintegrating agents and colouring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages. Oral fluids such as solution, syrups and elixirs can be prepared in dosage unit form so that a given quantity contains a predetermined amount of the compound. Syrups can be prepared by dissolving the compound in a suitably flavoured aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The composition can also be prepared to prolong or sustain the release as for example by coating or embedding particulate material in polymers, wax or the like.

The compounds suitable as a JMJD3/UTX inhibitor or a pharmaceutically acceptable salt thereof may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils. For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas. Dosage forms for nasal or inhaled administration may conveniently be formulated as aerosols, solutions, suspensions drops, gels or dry powders.

For compositions suitable and/or adapted for inhaled administration, it is preferred that the agent is in a particle-size-reduced form, and more preferably the size-reduced form is obtained or obtainable by micronization. The preferable particle size of the size-reduced (e.g. micronized) compound or salt or solvate is defined by a D50 value of about 0.5 to about 10 microns (for example as measured using laser diffraction). Compositions adapted for administration by inhalation include the particle dusts or mists. Suitable compositions wherein the carrier is a liquid for administration as a nasal spray or drops include aqueous or oil solutions/suspensions of the active ingredient which may be generated by means of various types of metered dose pressurized aerosols, nebulizers or insufflators.

Aerosol formulations, e.g. for inhaled administration, can comprise a solution or fine suspension of the agent in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurized aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the agent, (preferably in particle-size-reduced form, e.g. in micronized form), and optionally a performance modifier such as L-leucine or another amino acid, cellobiose octaacetate and/or metals salts of stearic acid such as magnesium or calcium stearate. Aerosol formulations are preferably arranged so that each metered dose or "puff of aerosol contains a particular amount of a compound of the invention. Administration may be once daily or several times daily, for example 2, 3 4 or 8 times, giving for example 1, 2 or 3 doses each time. The overall daily dose and the metered dose delivered by capsules and cartridges in an inhaler or insufflator will generally be double those with aerosol formulations.

Pharmaceutical compositions adapted for vaginal administration may be presented as pessaries, tampons, creams, gels, pastes, foams or spray formulations. Pharmaceutical compositions adapted for parental administration include aqueous and non-aqueous sterile injection solutions which may contain anti-oxidants, buffers, bacteriostats and solutes which render the composition isotonic with the blood of the intended recipient; and aqueous and nonaqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the compositions may include other agents conventional in the art having regard to the type of formulation in question, for example those suitable for oral administration may include flavouring agents.

To further review compounds in this class, we evaluated GSKJ1, GSKJ2, GSKJ4, and GSKJ5. Based on our data, and review of the molecule, the highly polar carboxylate group of GSKJ1 and GSKJ2 restricts cellular permeability. This poses potential problems for therapeutic administration, and indeed, our data shows that by masking the polarity of the acid groups of both the GSKJ1 and GSKJ2 with an ethyl ester, we yield GSKJ4 and GSKJ5 and greater efficacy.

GSKJ4 increased bioavailability, while GSKJ5 was inactive. In in vitro studies, though GSKJ1 and GSKJ2 remain potent over a control (data not shown). Accordingly, for purposes of treating disease and disorders here, the most preferred active pharmaceutical compound is GSK-J4.

The formula for GSK-J4 is:

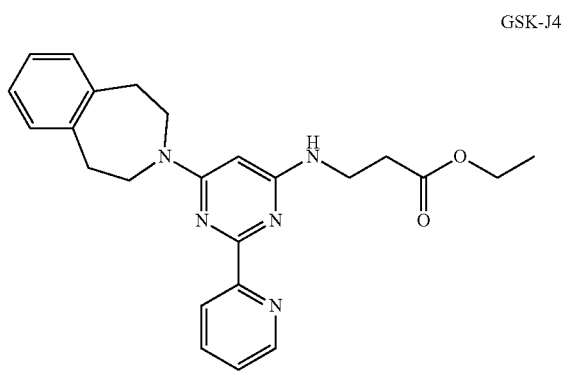 [SMILES: CCOC(=O)CCNc1cc(N2CCc3ccccc3CC2)nc(-c2ccccn2)n1]

GSK-J4

Accordingly, a method of preventing or reducing the formation of fibrosis comprises administering to a patient in need thereof, an effective amount of a histone H3K27 trimethylase (KDM) UTX inhibitor. Preferably, the inhibitor is GSK-J4.

We can also prevent the emergence of αSMA+ myofibroblasts by inhibiting UTX activity through administration of an effective amount of a UTX inhibitor, preferably GSKJ4.

We can also prevent the formation of excessive extracellular matrix production in many cases by administering to the patient an effective amount of an UTX inhibitor GSK-J4. For example, a preferred method of treatment includes where a medical practitioner must cut or penetrate the skin of a patient, such as in a surgical procedure, and administering to the patient having said surgical procedure, an effective amount of an UTX inhibitor, suitable to increase the number of H3K27me3 and thereby reducing the formation of excessive extracellular matrix.

A method of reducing the formation of fibrosis in a patient comprising blocking the enzymatic activities of UTX and JMJD3 by administering to said patient an effective amount of a UTX and JMJD3 inhibitor GSKJ4.

A method of preventing the onset and progression of a fibrotic disease by blocking pro-fibrotic transcription factors from binding to chromatin, comprising administering an effective amount of a therapeutic GSKJ4 sufficient to prevent the binding of pro-fibrotic transcription factor MRTF-A.

A method of treating or preventing the onset of fibrosis after a surgical procedure comprising: Performing a surgical procedure on a patient; administering to said patient an effective amount of a UTX and JMJD3 inhibitor. Preferably, the UTX and JMJD3 inhibitor is administered within 24 hours of the surgical procedure, and more preferably the UTX and JMJD3 inhibitor is administered to the patient within 16, 8, 4, 3, 2, 1 hour, or within 30 minutes, 15 minutes, 5 minutes, or simultaneously with the surgical procedure. Furthermore, re-administration of a further dose, or a sustained release dose is provided to maintain elevated levels of the inhibitor for a period of about 12-72 hours, preferably for about 12-48 hours, and more preferably for at least 24 hours.

For example, a patient is undergoing cataract surgery of the eye, it would be advantageous to perform the surgery and then provide the UTX and JMJD3 inhibitor to the patient during and after the procedure, but not more than 24 hours after the completion of the procedure. This allows for accumulation of H3K27me3, and thus allows the H3K27me3 to bind to the chromatin and generate or maintain a closed chromatin structure. Preferably, the UTX and JMJD3 inhibitor is GSKJ4, and is applied topically to the eye during the surgical procedure. A further step for such cataract surgery is the placement of an intra ocular lens, the IOC may be coated with a powder, suspension, or gel, or other delivery vehicle, to allow for delivery of the therapeutic to the eye for a sufficient period to prevent fibrosis formation. Preferably, this includes a period of at least the time from surgery to a period of about 24 hours after surgery. While additional exposure may be suitable, i.e. treatment for 3-7 days, the short treatment protocol is advantageous.

A preferred embodiment is directed to preventing or reducing the formation of fibrosis after a surgical procedure, comprising performing a surgical procedure, administering to the patient and effective amount of a UTX and JMJD3 inhibitor within 24 hours of the surgical procedure. Preferably, the UTX and JMJD3 inhibitor is provided at the time of the surgical procedure and is given for about 24 hours. For example, for a procedure on the eye, a topical administration may be provided at the time of the procedure and then given at least one additional time within the next 24 hour period. A short treatment is surprisingly effective over this 24 hour period to reduce and prevent the formation of fibrosis.

For example, when administering GSK-J4 to a patient, an appropriate therapeutic range comprises: about 1 μM to 10 μM concentration for a liquid, topical vehicle. Suitable doses can be generated based upon the tissue to be treated and area to be treated. Testing at the lower end of the range revealed that there was higher efficacy at 10 μM than the 1 μM, however, a further 10× increase to 100 μM began to show signs of toxicity. The LD50 is otherwise known to those of skill in the art based upon the molecule of interest. The GSK-J4 can be formulated with suitable excipients and into a suitable vehicle for delivery to a human patient.

A preferred embodiment comprises administration of a H3K27 de-methylase UTX inhibitor during and after a surgical procedure for 24 hours, sufficient to reduce or prevent the formation of fibrosis due to said surgical procedure. Preferably, the process includes administering to the patient undergoing the surgical procedure, an effective amount of said UTX inhibitor during the surgical process and at least one further dose of said UTX inhibitor within 24 hours of the surgical process. The benefit of the short timeframe is that the UTX inhibitor is effective to prevent re-programming of myofibroblast cells within this brief window is sufficient to prevent the re-programming and also allows for healing of the wound.

Depending on the surgical procedure, it may be suitable to administer a crème, gel, paste, suspension, or emulsion, in a pharmaceutically suitable carrier to the site of the surgical procedure. For example, an ocular surgery may use a direct application to the eye, the eye ducts and the like, wherein the active pharmaceutical material will reach the eye tissues that are at risk for becoming fibrotic. Similarly, a surgical procedure that requires an incision to the body may utilize a similar topical material, to prevent or reduce fibrosis formation at the incision site. Furthermore, in each the eye or the incision procedures, the pharmaceutical composition may be administered intradermally, through injection with a hypodermic needle to the skin tissues surrounding the skin tissues undergoing the surgical procedure.

Indeed, for procedures within the body, for example repaid or a ruptured tendon or major muscle tear, requiring surgical intervention, the internal tissues may be disposed to fibrosis. Accordingly, intramuscular injections of a pharmaceutical composition to the wound, injury, or surgical site will be effective for treating or preventing the formation of fibrosis. Surgeons of ordinary skill will be able to effectively administer the pharmaceutical composition into these wound sites and to choose the proper delivery vehicle, including injectable, solid, gel, paste, or other compositions formulated for internal delivery to the body.

Finally, for certain internal applications, it may be more effective for an oral application or inhaled application of the pharmaceutical composition. In such a case, an oral dosage form can be administered during a short treatment, typically for the first 24 hours after the surgical procedure.

Accordingly, the processes and methods described herein provide a therapeutic use of a pharmaceutical composition an inhibitor of UTX and/or JMJD3, preferably GSK-J4. Use of the inhibitor is effective in ensuring a condensed structure of chromatin and preventing the re-programming of myofibroblasts into a fibrotic cell. Accordingly, the therapeutic use of the pharmaceutical composition is effective in preventing or reducing the formation of fibrotic tissues.

What is claimed is:

1. A method of reducing tissue fibrosis, comprising:
   administering an effective amount of a pharmaceutical composition comprising at least one lysine 27 of histone H3 (H3K27) de-methylase UTX inhibitor selected from the group consisting of GSK-J2, GSK-J4, GSK-J5, and suitable salts thereof, to tissue having an open chromatin structure, and,
   closing the open chromatin structure via the accumulation of tri-methylated lysine 27 of Histone 3 (H3K27me3).

2. The method of claim 1, wherein the pharmaceutical composition is administered topically to a skin surface.

3. The method of claim 1, wherein the at least one H3K27 de-methylase UTX inhibitor in the pharmaceutical composition has a concentration of between 1 μM and 10 μM.

4. The method of claim 3, wherein the at least one H3K27 de-methylase UTX inhibitor in the pharmaceutical composition has a concentration of 10 μM.

5. The method of claim 1, wherein the pharmaceutical composition is administered to a patient within 24 hours of a surgical procedure.

6. The method of claim 1, wherein the pharmaceutical composition is administered to a patient at the time of surgery.

7. The method of claim 5, wherein the administering is performed before a fibrotic process establishes after the surgical procedure.

8. The method of claim 1, wherein the tissue is ocular tissue.

9. The method of claim 1, wherein reducing tissue fibrosis includes reducing fibrotic disease Posterior Capsule Opacification (PCO).

10. A method of treatment comprising administering to tissue in a patient undergoing a surgical procedure an effective amount of a pharmaceutical composition at the time of the surgical procedure, the composition comprising at least one lysine 27 of histone H3 (H3K27) de-methylase UTX inhibitor selected from the group consisting of GSK-J2, GSK-J4, GSK-J5, and suitable salts thereof, wherein the method includes: administering the pharmaceutical composition to tissue having an open chromatin structure and closing the open chromatin structure via the accumulation of tri-methylated lysine 27 of Histone 3 (H3K27me3).

11. The method of claim 10, wherein the pharmaceutical composition is administered orally, intradermally, or topically to a skin surface.

12. The method of claim 10, wherein the at least one H3K27 de-methylase UTX inhibitor in the pharmaceutical composition has a concentration of between 1 μM and 10 μM.

13. The method of claim 12, wherein the at least one H3K27 de-methylase UTX inhibitor in the pharmaceutical composition has a concentration of 10 μM.

14. A method of reducing fibrosis associated with ocular tissue due to ocular surgery, comprising:
   administering an effective amount of a pharmaceutical composition comprising at least one lysine 27 of histone H3 (H3K27) de-methylase UTX inhibitor selected from the group consisting of GSK-J2, GSK-J4, GSK-J5, and suitable salts thereof, to eye tissue having an open chromatin structure, and
   closing the open chromatin structure via the accumulation of tri-methylated lysine 27 of Histone 3 (H3K27me3).

15. The method of claim 14, wherein the pharmaceutical composition is administered topically to the eye during a surgical procedure.

16. The method of claim 14, wherein administering the pharmaceutical composition includes placing an intra ocular lens to the eye tissue for a period of at least the time from surgery to a period of about 24 hours after surgery.

17. The method of claim 16, wherein administering the pharmaceutical composition includes the intra ocular lens being coated with a powder, suspension, or gel.

18. The method of claim 14, wherein the at least one H3K27 de-methylase UTX inhibitor in the pharmaceutical composition has a concentration of between 1 μM and 10 μM.

19. The method of claim 18, wherein the at least one H3K27 de-methylase UTX inhibitor in the pharmaceutical composition has a concentration of 10 μM.

* * * * *